US008034583B2

(12) United States Patent
Dodge et al.

(10) Patent No.: US 8,034,583 B2
(45) Date of Patent: Oct. 11, 2011

(54) METABOLICALLY ENGINEERED BACTERIAL STRAINS HAVING NON-FUNCTIONAL ENDOGENOUS GLUCONATE TRANSPORTERS

(75) Inventors: Timothy C. Dodge, Sunnyvale, CA (US); Manoj Kumar, Fremont, CA (US); M. Harunur Rashid, Sunnyvale, CA (US); Fernando Valle, Burlingame, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/141,522

(22) Filed: Jun. 18, 2008

(65) Prior Publication Data

US 2008/0299614 A1    Dec. 4, 2008

Related U.S. Application Data

(62) Division of application No. 10/842,929, filed on May 10, 2004, now Pat. No. 7,419,795.

(60) Provisional application No. 60/473,310, filed on May 22, 2003, provisional application No. 60/478,056, filed on Jun. 11, 2003.

(51) Int. Cl.
*C12P 21/06* (2006.01)
(52) U.S. Cl. .................. 435/69.1; 435/320; 435/252.3; 435/471; 435/7.1; 536/23.7; 536/23.1; 530/350; 530/300
(58) Field of Classification Search ........................ None
See application file for complete search history.

(56) References Cited

U.S. PATENT DOCUMENTS

| | | | |
|---|---|---|---|
| 4,757,012 A | 7/1988 | Estell et al. | |
| 4,758,514 A | 7/1988 | Light et al. | |
| 4,760,025 A | 7/1988 | Estell et al. | |
| 5,004,690 A | 4/1991 | Light et al. | |
| 5,008,193 A | 4/1991 | Anderson et al. | |
| 5,032,514 A | 7/1991 | Anderson et al. | |
| 5,376,544 A | 12/1994 | Lazarus et al. | |
| 5,583,025 A | 12/1996 | Lazarus et al. | |
| 5,795,761 A | 8/1998 | Powers et al. | |
| 7,419,795 B2 * | 9/2008 | Dodge et al. ................... | 435/7.6 |

FOREIGN PATENT DOCUMENTS

| | | |
|---|---|---|
| JP | 426860 | 9/1992 |
| WO | WO 02/12468 | 2/2002 |
| WO | WO 02/12481 | 2/2002 |
| WO | WO 02/12528 | 2/2002 |
| WO | WO 02/81440 | 4/2002 |

OTHER PUBLICATIONS

Adachi, O. et al., "Crystallization and Characterization of NADP-Dependent D-Glucose Dehydrogenase from Gluconobacter suboxydans," (1980) *Agric. Biol. Chem*, 44 :301-308.
Ameyama, M. et al., "D-Glucose Dehydrogenase of Gluconobacter suboxydans : Solubilization, Purification and Characgerization," (1981) *Agric. Biol. Chem.* 45 :851-861.
Anderson et al., "Production of 2-Keto-L-Gulonate, an Intermediate in L-Ascorbate Synthesis, by a Genetically Modified *Erwinia herbicola*," *Science*, vol. 230, Oct. 11, 1985, pp. 144-149.
Balbas et al., "A pBRINT family of plasmids for integration of cloned DNA into the *Escherichia coli* chromosome," *Gene*, (1996) 172 :65-69.
Barredo et al. "Glucokinase-Deficient of Penicillium chrysogenum is Derepressed on Glucose Catabolite Regulation of Both β-Galactosidase and Penicillin Biosynthesis," Antimicrob. Agents-Chemother 32: 1061-1067, (1988).
Bausch et al., Sequence analysis of the Gntll (subsidiary) system for gluconate metabolism reveals a novel pathway for L-idonic acid catabolism in *Escherichia coli, J. of Bacteriology*, V. 180(14), Jul. 1998, pp. 3704-3710.
Chen et al., "Nested PCR with Three Highly Degenerate Primers for Amplication and Identification of DNA from Related Organisms," *Biotechniques*, (1995) 18(4) :609-612.
Bunton et al., "The Determination of Ascorbic and Erythorbic Acids in Meat Products," *J. Assoc. Pub. Analysts*, (1979), 17:105.
DiMarco et al "D-Glucose Transport System of Zymomonas mobilis," Appl. Environ. Microbiol. 49:151-157, (1985).
Frey et al., The Molecular biology of IncQ plasmids. In: Thomas (Ed.), *Promiscuous Plasmids of Gram Negative Bacteria*. Academic Press, London, pp. 79-94, (1989).
Frey et al., "Replication and copy number control of the broad-host-range plasmid RSF1010," Gene 113:101-106, (1992).
Grindley et al., "Conversion of Glucose to 2-Keto-L-Gluconate, an Intermediate in L-Ascorbate Synthesis, by a Recombinant Strain of *Ervinia citreus*," Applied and Environmental Microbiology 54: 1770-1775, (1988).
Harrod et al., "Derepressed utilization of L-malic acid and succinic acid by mutants of *Pachysolen tannophilus,*" *J. Ind. Microbiol. Biotechnol.* 18:379-383, (1997).
Kageyama et al. "*Pantoea punctata* sp. nov., *Pantoea citrea* sp. nov., and *Pantoea terra* sp. nov. Isolated from Fruit and Soil Samples," *International Journal of Systematic Bacteriology* vol. 42, p. 203-210, (1992).
Kramer et al., "The gapped duplex DNA to oligonucleotide-directed mutation construction," Nucleic Acids Res. 12:9441, (1984).
Le Borgne et al., "pBRINT-T$_s$: a plasmid family with a temperature-sensitive replicon, designed for chromosomal integration into the lacZ gene of *Escherichia coli,*" *Gene*, (1998) 223:213-219.
Lerner et al., "Low copy number plasmids for regulated low-level expression of cloned genes in *Escherichia coli* with blue/white insert screening capability," *Nucleic Acids Res.*, vol. 18, No. 15, pp. 4631, 1990.
Matsushita et al., "Membrane-Bound D-Gluconate Dehydrogenase from," J. Biochem. 85:1173-1181, (1979).
McIntire et al., "Identification of the covalently bound flavins of D-gluconate dehydrogenases from *Pseudomonas aeruginosa* and *Pseudomonas fluorescens* and of 2-keto-D-gluconate de hydrogenase from *Gluconobacter melanogenus*", Biochem.J.(1985), 231, 651-654.

(Continued)

*Primary Examiner* — Hope Robinson

(57) ABSTRACT

The present invention relates to engineering metabolic pathways in bacterial host cells which results in enhanced carbon flow for the production of ascorbic acid (ASA) intermediates. In particular, the invention relates to increasing the production of ASA intermediates in bacterial cells by enhancing the availability of gluconate resulting from the inactivation of endogenous gluconate transporter genes.

7 Claims, 8 Drawing Sheets

OTHER PUBLICATIONS

Miller et al., "A Novel Suicide Vector and its Use in Construction of Insertion Mutations: Osmoregulation of Outer Membrane Proteins and Virulence Determinants in *Vibrio cholerae* Requires toxR," J. Bacteriol. 170, 2575-2583, (1988).

Moring et al Should Be Morinaga, et al. "Improvement of Oligonucleotide-Directed Site-Specific Mutagenesis Using Double-Stranded Plasmid DNA", *Biotech*. 2:636-639 (1984).

Neijssel et al., "Physiological Significance and Bioenergetic Aspects of Glucose Dehydrogenase," Antonie Van Leauvenhoek, 56(1):51-61, 1989.

Pachla et al., "Determination of Ascorbic Acid in Foodstuffs, Pharmaceuticals, and Body Fluids by Liquid Chromatography with Electrochemical Detection", *Analytical Chemistry*, vol. 48, No. 2, Feb. 1976, pp. 364-367.

Palmeros et al., "A family of removable cassettes designed to obtain antibiotic-resistance-free genomic modifications of *Escherichia coli* and other bacteria," *Gene*, 247, 255-264, (2000).

Peekhaus, et al., Characterization of a novel transporter family that includes multiple *Escherichia coli* gluconate transporters and their homologues, *Fems Microbiology Letters*, V. 147(2), 1997, pp. 233-238.

Potter, Huntington, << Electroporation in Biology: Methods, Applications, and Instrumentation, >> Analytical Biochemistry, vol. 174, pp. 361-373, 1988.

Reichstein and Grussner, Eine ergiebige Synthese der I-Ascorbinsaure (C-Vitamin)2) Helv. Chem. Acta., 17, 311-328 (1934).

Reichstein T. et al., "Die Synthese der d-Ascorbinsaure (d-Form des C-Vitamins)," (1933) *Helv. Chim. Acta.* 16: 561, 1019).

Reizer et al., "Analysis of the gluconate (gnt) operon of *Bacillus subtilis*," (1991) *Mol. Microbiol*. 5:1081-1089.

Russell et al., "Carbohydrate Metabolism in the Mosquito Pathogen *Bacillus sphaericus* 2362," (1989) *Appl. Environ. Microbiol*. 55: 294-297.

Shinagawa, E. et al., "Distribution and Solubilization of Particulate Gluconate Dehydrogenase and particulate 2-Ketogluconate Dehydrogenase in Acetic Acid Bacteria," (1976) *Agric. Biol. Chem.* 40:475-483.

Shinagawa, E. et al., "Distribution of Gluconate Dehydrogenase and Ketogluconate Reductases in Aerobic Bacteria," (1978) *Agric. Biol. Chem.* 42:1055-1057.

Shinagawa, E. et al., "Purification and Characterization of 2-Keto-D-gluconate Dehydorgenase from *Gluconbacter melanogenus*," (1981) *Agric. Biol. Chem.*, 45:1079-1085.

Smith et al., "Purification and characterization of glucose dehydrogenase from the thermoacidophilic archaebacterium *Thermoplasma acidophilum*," Biochem. J., 261:973, (1989).

Stroshane et al., "Fermentation of Glucose by *Acetobacter melanogeuns*," Biotechnol. BioEng., 19(4) 459, (1977).

Truesdell, et al., "Pathways for Metabolism of Ketoaldonic Acid in an *Erwinia* sp." Journal of Bacteriology, 173:6651-6656, (1991).

Tsunedomi et al., << The Activator of GntII Genes for Gluconate Metabolism, GntH, Exerts Negative Control of GntR-Regulated GntI Genes in *Escherichia coli, J. of Bact.*, V. 185, N. 6, pp. 1783-1795, Mar. 2003.

Walsh et al. "Cloning of genes that Complement Yeast Hexokinase and Glucokinase Mutants," J. Bacteriol. 154:1002-1004, (1983).

Wedlock, et al. "A Hexokinase Associated with Catabolite Repression in *Pachysolen tannophilus*," J. Gen. Microbiol. 135: 2013-2018, (1989).

Yamada et al., "Analysis of the *Escherichia coli* gntT and gntU Genes and Comparison of the Products with Their Homologues," *Biosci. Biotech. Biochem.*, 60 (9), 1548-1550, 1996.

* cited by examiner

SEQ ID NO: 1 - Nucleic Acid Sequence for a
*Pantoea citrea* Gluconate Transporter Gene (*gntU*).

```
ATGATAAGTACCGCAACACTGGTGCTAACCGCAGCCGGATCAGTTCTGCTGCTGTTACTG
CTGGTTATGAAAGCCAGGATGCATGCTTTTGTCGCTTTAATGTTAGTCTCCGTGGGTGCCGG
GATGATGTCCGGAATGCCACTGATAAAAATTACTGAAACCATGCAAAAAGGCATGGGTGGCA
CTCTTGGCTTTCTGGCCATTGTGGTCGCACTGGGAGCCATGTTCGGAAAAATTCTGCATGAA
ACCGGGGCTGTCGATCAGATTGCTATCCGCATGCTGAAAACCTTTGGTGAAAAACGGGCGCA
CTATGCGATGGGTATTGCCGGATTTATCTGTGCATTGCCGTTATTTTTTGAAGTGGCCATTG
TATTGCTGATAAGCATTGCGTTTGCTGTTGCCAGACGTACTGGTGGCAATCTGGTGAAACTG
GTGATTCCGTTGTTTGCCGGGGTTGCGGCGGCAGCGGCTTTTGTACTGCCGGGGCCAGCTCC
AATGCTACTGGCCTCGCAGATGCATGCTGATTTTGGCTGGATGATCCTGATAGGGTTATGTG
CAGCCATCCCTGGCATGTTGATTGCCGGTCCGTTGTTTGGCAGCTTTATTTCCCGACATGTT
CACTTTTCTCTGCCTGCCGAAGATACTCAGCCGCAAGTTGAAGCCCATAAGCTCCCCTCTTT
TGGTTTTAGCCTGTCACTGATCCTGTTTCCGCTGGTGCTGGTAGGGCTAAAAACTATCGGCG
CACATTTTGTGGCTGCCGGAACTCCGGTATACAACTTCCTGGAGTTTATTGGTCATCCGTTT
ATTGCGATTCTGCTGGCCTGTCTGATCACCATCTATGGTCTGGCGTATCGTCAGGGGATGGA
TAAATCACGGATTATGCAGATCTGCGGGGAAGCGCTACAACCTGCCGGTATTATTCTGCTGG
TGATTGGTGCGGGTGGGGTATTTAAACAGGTACTGGTGGATTCCGGAGTAGGTCCGGCACTG
GGTGATGCCGTTGCAGGTGCCGGATTACCGGTGGCTGTGGCCTGTTTTATCCTGGCGGGTGC
TGTCAGGATCATTCAGGGTTCTGCGACTGTTGCCTGTCTGACGGCAGTCGGACTGATTATGC
CGGTGATCGAACCGTTGCATTACAGTGGTGCTCAGCTGGCTGCACTTTCTGTCTGTATTGGC
GGTGGATCGATTATTTTCAGCCATGTGAATGACGCTGGTTTCTGGTTATTTGGTCGTTTTAC
CGGAGCCTCAGAAGCCGAAACACTGAAGACCTGGACGTTGATGGAAACTATTCTCGGAACCA
GTGGTGGCATCATTGGCATGCTGGCCTTCTGGCTGCTGAGC
```

FIG. 3

SEQ ID NO: 2 - Amino Acid Sequence for a
*Pantoea citrea* Gluconate Transporter Protein (*GntU*)

```
MISTATLVLTAAGSVLLLLLVMKARMHAFVALMLVSVGAGMMSGMPLIKITETMQKGMGGT
LGFLAIVVALGAMFGKILHETGAVDQIAIRMLKTFGEKRAHYAMGIAGFICALPLFFEVAIV
LLISIAFAVARRTGGNLVKLVIPLFAGVAAAAAFVLPGPAPMLLASQMHADFGWMILIGLCA
AIPGMLIAGPLFGSFISRHVHFSLPAEDTQPQVEAHKLPSFGFSLSLILFPLVLVGLKTIGA
HFVAAGTPVYNFLEFIGHPFIAILLACLITIYGLAYRQGMDKSRIMQICGEALQPAGIILLV
IGAGGVFKQVLVDSGVGPALGDAVAGAGLPVAVACFILAGAVRIIQGSATVACLTAVGLIMP
VIEPLHYSGAQLAALSVCIGGGSIIFSHVNDAGFWLFGRFTGASEAETLKTWTLMETILGTS
GGIIGMLAFWLLS
```

FIG. 4

SEQ ID NO: 3 - Nucleic Acid Sequence for a
Pantoea citrea Gluconate Transporter Gene (idnT).

ATGCCAATTACAATAATAGCGCTCGGGGTAATACTGCTGCTGGTCCTGATGATTGTTTTC
AAGGCCAACGGCTTTTTATCTCTGATTTTTGTCTCCATCGTCGTAGGTATAGCCGAAGGG
ATGACACCGTTGCAGGCCCTGGCTTCTGTACAAAAAGGGGTTGGCGGTACTCTGGGCAGC
CTTGCGATGATTCTTGGTTTTGGTGCCATGCTCGGTAAGCTGGTGTCAGATACCGGGGCC
GCCCAACGGGTGGCGACCACGTTGATTGCGGCTTTTGGTAAACAGCGGGTGCAATGGGCT
CTGATGGTGACAGGGCTGATTGTCGGGCTGGCCATGTTTTATGAAATTGGTTTTGTCCTG
TTGTTACCGCTGGTGTTTACCGTGGTGGCCGCCGCCGGTATGCCATTACTGTATGTGGGG
CTGCCGATGGTGGCTGCATTGTCAGTGACCCATTGCTTCCTGCCTCCGCACCCGGGGCCG
ACGGCGATCGCCGCTATCTTCGGGGCCAATCTGGGTACCACACTGTTGTATGGCATAATT
ATTACCCTGCCAACGGTGATTGTGGCCGGTCCGGTATTTTCTAAGTTCCTAAAAAACTTT
GAAAAGAACCGCCGGAAGGGCTGTATAACCCCAAAATTTTCGCCGAACATGAGTTGCCC
GGATTCGCTATTAGTATATTTGCTGCAGTCATCCCGGTGATCCTTATGGCGATTGCCGCA
GTTTTTGAACTCACAACTCCGAAAGAGAATCCGCTCCGTCAGTTTTTCGAATTTATTGGT
AACCCTGCGATCGCGCTGTTTATTGCCGTGGTGATCGCCGTATTTACCCTCGGATTGCGC
AATGGCCGGAAAATGGGCGAAGTCATGGAGATGTGCAGCTCCTCAATTTCGTCAATTGCC
ATGATTGTATTTATCATTGCCGGTGGCGGGGCATTTAAACAAGTCCTGGTGGACAGTGGG
GTGGGCGATTTTATCGCAGGAATGATGAAAGGATCGTCATTGTCGCCACTATTGATGTGC
TGGACCGTGGCGGCAATGCTGCGAGTTGCGTTGGGATCAGCCACAGTAGCGGCGATTACT
ACCGCGGGTATTGTCACTCCGATTATCGCGGTGACTCACGCAGACCCTGCACTAATGGTG
TTGGCGGTAGGGTCTGGTAGCGTGATCGCCTCGCATGTTAATGACCCCGGTTTCTGGTTA
TTCAAAGGCTACTTTAATCTGAGCGTGACTGAAACACTGAAAACCTGGACTGTGATGGAA
ACACTGATTTCGGTGATGGGTCTGGCCGGAGTCCTTATTCTTAACTCAGTACTGCACTAA

FIG. 5

SEQ ID NO: 4 - Amino Acid Sequence for a
Pantoea citrea Gluconate Transporter Protein (idnT).

MPITIIALGVILLLVLMIVFKANGFLSLIFVSIVVGIAEGMTPLQALASVQKGVGGTLGS
LAMILGFGAMLGKLVSDTGAAQRVATTLIAAFGKQRVQWALMVTGLIVGLAMFYEIGFVL
LLPLVFTVVAAAGMPLLYVGLPMVAALSVTHCFLPPHPGPTAIAAIFGANLGTTLLYGII
ITLPTVIVAGPVFSKFLKNFEKEPPEGLYNPKIFAEHELPGFAISIFAAVIPVILMAIAA
VFELTTPKENPLRQFFEFIGNPAIALFIAVVIAVFTLGLRNGRKMGEVMEMCSSSISSIA
MIVFIIAGGGAFKQVLVDSGVGDFIAGMMKGSSLSPLLMCWTVAAMLRVALGSATVAAIT
TAGIVTPIIAVTHADPALMVLAVGSGSVIASHVNDPGFWLFKGYFNLSVTETLKTWTVME
TLISVMGLAGVLILNSVLH

FIG. 6

Percent Amino Acid Identity

| Transporter |   | 1 | 2 | 3 | 4 | 5 | 6 | 7 | 8 | 9 | 10 |
|---|---|---|---|---|---|---|---|---|---|---|---|
| Ec-yjhF | 1 |   | 30.3 | 34.5 | 46.2 | 46.9 | 30.5 | 58.5 | 32.4 | 44.6 | 31.6 |
| Ec-dsdX | 2 |   |   | 29.4 | 33.0 | 29.8 | 26.3 | 33.9 | 30.3 | 33.5 | 31.0 |
| Ec-gntP | 3 |   |   |   | 38.7 | 39.4 | 28.2 | 35.8 | 28.9 | 40.5 | 28.7 |
| Ec-gntT | 4 |   |   |   |   | 60.6 | 31.1 | 49.4 | 31.4 | 58.8 | 33.0 |
| Ec-idnT | 5 |   |   |   |   |   | 31.7 | 49.2 | 33.9 | 76.3 | 34.2 |
| Ec-o454 | 6 |   |   |   |   |   |   | 31.7 | 33.1 | 31.0 | 30.5 |
| Bs-gntP | 7 |   |   |   |   |   |   |   | 34.0 | 48.3 | 33.0 |
| Pc-gntU | 8 |   |   |   |   |   |   |   |   | 33.0 | 78.0 |
| Pc-idnT | 9 |   |   |   |   |   |   |   |   |   | 32.8 |
| Ec-gntU | 10 |   |   |   |   |   |   |   |   |   |   |

METABOLICALLY ENGINEERED BACTERIAL STRAINS HAVING NON-FUNCTIONAL ENDOGENOUS GLUCONATE TRANSPORTERS

This is a divisional of application Ser. No. 10/842,929 filed on May 10, 2004 now U.S. Pat. No. 7,419,795.

The present application claims priority to U.S. Provisional Patent Application Ser. No. 60/473,310, filed May 22, 2003 and to U.S. Provisional Patent Application Ser. No. 60/478,056, filed Jun. 11, 2003.

FIELD OF THE INVENTION

The present invention relates to engineering metabolic pathways in bacterial host cells which results in enhanced carbon flow for the production of polyols and keto-derivatives thereof. More specifically the invention relates to the enhanced production of keto-polyols, such as sugar-keto acids and more specifically to ascorbic acid intermediates. In particular, the invention relates to enhancing the industrial production of gluconate, 2-keto-D-gluconic acid (KDG or 2-KDG), 2,5-diketogluconate (DKG or 2-DKG) and 2-keto-L-gulonic acid (KLG or 2-KLG) in *Pantoea* cells by altering an endogenous gluconate transporter. The invention further relates to altered *Pantoea* strains having one or more non-functional endogenous gluconate transporter genes and optionally inactivated endogenous glucokinase and/or gluconokinase genes.

BACKGROUND OF THE INVENTION

Numerous products of commercial interest, such as intermediates of L-ascorbic acid, have been produced biocatalytically in genetically engineered host cells. L-Ascorbic acid (vitamin C, ASA) is commonly used in the pharmaceutical and food industries as a vitamin and antioxidant, and due to this relatively large market volume and high value as a specialty chemical the synthesis of ASA has received considerable attention.

A chemical synthesis route from glucose to ASA, commonly known as the Reichstein-Grussner method, was first disclosed in 1934 (Reichstein T. et al., (1934) *Helv. Chim. Acta,* 17:311-328 and Reichstein T. et al. (1933) *Helv. Chim. Acta.* 16: 561, 1019). A bioconversion method for the production of an ASA intermediate, 2-KLG, has been disclosed by Lazarus et al. (1989, "Vitamin C: Bioconversion via a Recombinant DNA Approach", GENETICS AND MOLECULAR BIOLOGY OF INDUSTRIAL MICROORGANISMS, American Society for Microbiology, Washington D.C. Edited by C. L. Hershberger). This bioconversion of a carbon source to KLG involves a variety of intermediates, and the enzymatic process is associated with co-factor dependent 2,5-DKG reductase activity (DKGR). Additionally, recombinant DNA techniques have been used to bioconvert glucose to KLG in *Erwinia herbicola* in a single fermentative step (Anderson, S. et al., (1985) *Science* 230:144-149). Effective procedures for converting KLG to ASA are described in Crawford et al., ADVANCES IN CARBOHYDRATE CHEMISTRY AND BIOCHEMISTRY, 37:79-155 (1980).

A number of strategies have been explored in bacteria and other microorganisms to increase the production of ASA intermediates. Some of these strategies include; gene deletions, gene additions and random mutagenesis. In particular, some gene manipulation strategies are mentioned below and include: (i) overexpressing particular genes in the ASA pathway (Anderson et al., (1985) *Sci.* 230:144-149; Grindley et al., (1988) *Appl. Environ. Microbiol.* 54: 1770; and U.S. Pat. No. 5,376,544); (ii) mutating genes encoding glycolytic enzymes (Harrod, et al. (1997) *J. Ind. Microbiol. Biotechnol.* 18:379-383; Wedlock, et al. (1989) *J. Gen. Microbiol.* 135: 2013-2018; and Walsh et al. (1983) *J. Bacteriol.* 154:1002-1004); (iii) utilizing bacterial host strains deficient in glucokinase (Japanese patent publication JP 4267860; Russell et al. (1989) *Appl. Environ. Microbiol.* 55: 294-297; Barredo et al.(1988) *Antimicrob. Agents-Chemother* 32: 1061-1067; and DiMarco et al. (1985) *Appl. Environ. Microbiol.* 49:151-157); (iv) reducing metabolism of glucose or gluconate by deletion of a gene required for phosphorylation, for example deleting the glucokinase gene (glkA) or gluconokinase gene (gntK) (WO 02/081440); and (v) reducing metabolism by manipulating enzymes involved in carbon utilization downstream of the initial glucose phosphorylation, for example manipulating phosphoglucose isomerase, phosphofructokinase, glucose-6-phosphate dehydrogenase, 6-phosphogluconate dehydrogenase or 6-phosphogluconate dehydratase.

Despite the above strategies, problems still persist concerning the diversion of ASA intermediates for catabolic metabolic purposes, and this results in reducing the efficiency and overall production of ASA intermediates. Thus, there still remains a need for improved production methods for ASA intermediates which are coupled to the metabolic pathways of host cells.

Carbon sources, such as glucose and gluconate, involved in the production of ASA intermediates may be separated by a cellular membrane from the reactions which utilize these substrates. When such a substrate and the synthetic machinery are separated, production of the product may require translocation of the substrate to the site of the synthetic reaction. Alternatively products generated inside the cell may require translocation from within the cell. Therefore, altering a substrate transport system may result in increased or decreased substrate availability for a particular metabolic pathway.

The present invention provides altered bacterial strains which include non-functional gluconate transporter molecules. The altered bacterial strains, which include the non-functional transporter molecules, have an increased amount of carbon substrate, such as glucose that may be utilized for the production of desired products, such as ASA intermediates.

SUMMARY OF THE INVENTION

The present invention provides methods of producing a desired product which comprises manipulating bacterial host cells to reduce carbon substrate diverted to metabolic pathways, thus increasing the productivity of the host cell for a desired product. Such manipulated bacterial host cells when cultured in the presence of a carbon source demonstrate increased yield of a desired product as measured directly and/or indirectly.

In one aspect, the invention provides isolated polynucleotides encoding polypeptides isolated from a strain of *Pantoea* having gluconate transporter activity. In one embodiment, the isolated polynucleotide comprises a nucleotide sequence having at least 40% sequence identity to a nucleotide sequence selected from the group consisting of SEQ ID NO: 1 and SEQ ID NO: 3. In a second embodiment, the isolated polynucleotide comprises a nucleotide sequence having at least 80% sequence identity to a nucleotide sequence selected from the group consisting of SEQ ID NO: 1 and SEQ ID NO: 3. In a third embodiment, the isolated polynucleotide comprises the nucleotide sequence of SEQ ID NO: 1 or SEQ ID NO: 3. In a fourth embodiment, the isolated polynucleotide comprises a nucleotide sequence which encodes a gluconate transporter having an amino acid sequence at least 40% identical to the sequence of SEQ ID NO: 2. In a fifth embodiment, the isolated polynucleotide comprises a nucleotide sequence which encodes a gluconate transporter having an amino acid sequence at least 80% identical to the sequence of SEQ ID NO: 2. In a sixth embodiment, the isolated polynucleotide comprises a nucleotide sequence which encodes a gluconate transporter having an amino acid sequence at least 80% identical to the sequence of SEQ ID NO: 4. In a seventh embodiment, the isolated polynucleotide comprises a nucleotide sequence which encodes a gluconate transporter having an amino acid sequence at least 90% identical to the sequence of SEQ ID NO: 4. In an eighth embodiment the isolated polynucleotide encodes a gluconate transporter having the sequence of SEQ ID NO: 2 or SEQ ID NO:4.

In another aspect, the invention relates to an isolated gluconate transporter protein comprising an amino acid sequence shown in SEQ ID NO: 2 or an amino acid sequence having at least 80% amino acid sequence identity thereto. In one embodiment, the isolated gluconate transporter protein has been isolated from *Pantoea*. In a second embodiment, the isolated gluconate transporter protein has the sequence shown in SEQ ID NO: 2.

In a further aspect, the invention relates to an isolated gluconate transporter protein comprising an amino acid sequence shown in SEQ ID NO: 4 or an amino acid sequence having at least 80% amino acid sequence identity thereto. In one embodiment, the isolated gluconate transporter protein has been isolated from *Pantoea*. In a second embodiment, the isolated gluconate transporter protein has the sequence shown in SEQ ID NO: 4.

In another aspect, the present invention provides a method for enhancing the level of production of an ascorbic acid (ASA) intermediate comprising, obtaining an altered bacterial host cell which is capable of producing an ASA intermediate, wherein an endogenous gluconate transporter gene has been rendered non-functional, culturing the altered bacterial host cell under suitable culture conditions in the presence of a carbon source to allow the production of an ASA intermediate and obtaining the ASA intermediate, wherein the level of production of the ASA intermediate is enhanced compared to the level of production of the ASA intermediate in a corresponding unaltered bacterial cell grown under essentially the same conditions. In one embodiment of the process, the endogenous gluconate transporter has at least 40% sequence identity to the amino acid sequence of SEQ ID NO: 2 or at least 80% sequence identity to the amino acid sequence of SEQ ID NO: 4. In a second embodiment of the process, the bacterial host cell is altered to include two non-functional gluconate transporter genes. In a third embodiment of the process, the gluconate transporter gene is deleted from the host chromosome. In a fourth embodiment, the process further comprises the step of isolating the ASA intermediate. In a fifth embodiment, the process further comprises converting the ASA into a second product. In a sixth embodiment, the host cell is an Enterobacteriaceae cell. In a seventh embodiment of the process, the endogenous gluconate transporter gene encodes a protein having at least 80% sequence identity to the sequence of SEQ ID NO: 2 or SEQ ID NO: 4. In an eighth embodiment of the process, the gluconate transporter gene encodes a protein designated GntU having the amino acid sequence of SEQ ID NO: 2. In an ninth embodiment of the process, the gluconate transporter gene encodes a protein designated IdnT having an amino acid sequence of SEQ ID NO: 4. In a tenth embodiment of the process, the bacterial host cell includes an inactivated glucokinase (glk) gene and/or an inactivated gluconokinase (gntK) gene. In an eleventh embodiment, the invention concerns an altered bacterial host cell produced by said process.

In a further aspect, the invention provides a recombinant Enterobacteriaceae strain comprising one or more nonfunctional endogenous gluconate transporter proteins. In one embodiment, the one or more non-functional endogenous gluconate transporter proteins has an amino acid sequence of at least 80% sequence identity to the sequence of SEQ ID NO: 2 or SEQ ID NO: 4. In further embodiments of this aspect the recombinant Enterobacteriaceae strain further comprises an inactivated endogenous glucokinase gene, an inactivated endogenous gluconokinase gene, and/or an overexpressed or heterologous DKG transporter genes. In a preferred embodiment, the recombinant strain is a *Pantoea* or *E. coli* strain.

In yet another aspect, the invention provides a recombinant *Pantoea* cell comprising an endogenous gluconate transporter gene which has been inactivated, wherein said gluconate transporter gene prior to being inactivated encoded a gluconate transporter protein comprising the amino acid sequence shown in SEQ ID NO: 2 or an amino acid sequence having at least 40% sequence identity thereto, wherein said protein functioned by transporting gluconate across a *Pantoea* cell membrane into the cytoplasm. In one embodiment, the recombinant *Pantoea* cell will include an inactivated endogenous glucokinase gene and in another embodiment the recombinant *Pantoea* cell will include a heterologous DKG transporter gene.

In another aspect, the invention provides an altered *Pantoea* cell comprising an inactivated endogenous gluconate transporter gene, wherein said gluconate transporter gene prior to being inactivated encoded a gluconate transporter protein comprising the amino acid sequence shown in SEQ ID NO: 4 or an amino acid sequence having at least 80% sequence identity thereto, wherein said protein functioned by transporting gluconate across a *Pantoea* cell membrane into the cytoplasm. In one embodiment, the altered *Pantoea* cell will include an inactivated glucokinase gene and in another embodiment the altered *Pantoea* cell will include a modified DKG transporter gene.

In a further aspect, the invention provides a method of enhancing the production of an ascorbic acid (ASA) intermediate from a carbon source comprising, obtaining a *Pantoea* host cell comprising an endogenous gluconate transporter gene which encodes a gluconate transporter protein having an amino acid sequence shown in SEQ ID NO: 2, SEQ ID NO: 4, or an amino acid sequence having at least 40% sequence identity to SEQ ID NO: 2 or SEQ ID NO: 4, altering the *Pantoea* host cell by rendering the gluconate transporter gene non-functional, wherein the altered *Pantoea* host cell is capable of producing an ASA intermediate in the presence of glucose, culturing said altered *Pantoea* host cell under suitable conditions in the presence of a carbon source, and allowing the production of an ASA intermediate from the carbon source, wherein the production of said ASA intermediate is enhanced in the altered *Pantoea* cell compared to the production of the ASA intermediate in an unaltered *Pantoea* host cell cultured under essentially the same culture conditions. In one embodiment of the method, the ASA intermediate is selected from the group consisting of gluconate, 2-keto-D-gluconate, 2,5-diketo-D-gluconate, 2-keto-L-gulonic acid and L-idonic acid. In a second embodiment, the ASA intermediate is further converted to erythorbic acid or tartrate. In a third embodiment, the gluconate transporter gene is gntU having the nucleic acid sequence illustrated by SEQ ID NO: 1 and/or idnT having the nucleic acid sequence illustrated in SEQ ID NO: 3.

In still another aspect, the invention provides a method of increasing the production of KLG in a *Pantoea* host cell which comprises obtaining a *Pantoea* host cell including a gluconate transporter gene which encodes a gluconate transporter having an amino acid sequence shown in SEQ ID NO: 2, SEQ ID NO: 4 or an amino acid sequence having at least 40% sequence identity to SEQ ID NO: 2 or SEQ ID NO: 4; altering the *Pantoea* host cell by rendering the gluconate transporter gene non-functional, wherein the altered *Pantoea* host cell is capable of producing KLG in the presence of glucose; culturing said altered *Pantoea* host cells under suitable conditions in the presence of a carbon source; and allowing the production of KLG from the carbon source, wherein the production of said KLG is enhanced in the altered *Pantoea* host cell compared to the production of KLG in an unaltered *Pantoea* host cell cultured under essentially the same culture conditions. In one embodiment, the invention relates to the altered *Pantoea* cell obtained according to the above method. In further embodiments, the method comprises a *Pantoea* cell genetically engineered to include a non-functional glucokinase gene, a non-functional gluconokinase gene and/or overexpressed DKG transporter genes.

In still another aspect, the invention provides a method of increasing the production or availability of gluconate in an oxidative pathway of a *Pantoea* host cell which comprises obtaining a *Pantoea* host cell including a gluconate transporter gene which encodes a gluconate transporter having an amino acid sequence shown in SEQ ID NO: 2, SEQ ID NO: 4 or an amino acid sequence having at least 40% sequence identity to SEQ ID NO: 2 or SEQ ID NO: 4; altering the *Pantoea* host cell by rendering the gluconate transporter gene non-functional, wherein the altered *Pantoea* host cell is capable of producing gluconate in the presence of glucose; culturing said altered *Pantoea* host cells under suitable conditions in the presence of a carbon source; and allowing the production of gluconate from the carbon source, wherein the production or availability of said gluconate in an oxidative pathway is enhanced in the altered *Pantoea* host cell compared to the production or availability of gluconate in an unaltered *Pantoea* host cell cultured under essentially the same culture conditions. In one embodiment, the invention relates to the altered *Pantoea* cell obtained according to the above method. In further embodiments, the method comprises a *Pantoea* cell genetically engineered to include a non-functional glucokinase gene, a non-functional gluconokinase gene and/or overexpressed DKG transport genes.

Another aspect of the invention provides a method of increasing the production of KDG in a *Pantoea* host cell which comprises obtaining a *Pantoea* host cell including a gluconate transporter gene which encodes a gluconate transporter having an amino acid sequence shown in SEQ ID NO: 2, SEQ ID NO: 4 or an amino acid sequence having at least 40% sequence identity to SEQ ID NO: 2 or SEQ ID NO: 4; altering the *Pantoea* host cell by rendering the gluconate transporter gene non-functional, wherein the altered *Pantoea* host cell is capable of producing KDG in the presence of glucose; culturing said altered *Pantoea* host cells under suitable conditions in the presence of a carbon source; and allowing the production of KDG from the carbon source, wherein the production of said KDLG is enhanced in the altered *Pantoea* host cell compared to the production of KDG in an unaltered *Pantoea* host cell cultured under essentially the same culture conditions. In one embodiment the invention relates to the altered *Pantoea* cell obtained according to the above method. In further embodiments, the method comprises a *Pantoea* cell genetically engineered to include a non-functional glucokinase gene, a non-functional gluconokinase gene and/or overexpressed DKG transport genes. In some embodiments, the invention includes the altered *Pantoea* host cells.

In still another aspect, the invention provides a method of increasing the production of DKG in a *Pantoea* host cell which comprises obtaining a *Pantoea* host cell including a gluconate transporter gene which encodes a gluconate transporter having an amino acid sequence shown in SEQ ID NO: 2, SEQ ID NO: 4 or an amino acid sequence having at least 40% sequence identity to SEQ ID NO: 2 or SEQ ID NO: 4; altering the *Pantoea* host cell by rendering the gluconate transporter gene non-functional, wherein the altered *Pantoea* host cell is capable of producing DKG in the presence of glucose; culturing said altered *Pantoea* host cells under suitable conditions in the presence of a carbon source; and allowing the production of DKG from the carbon source, wherein the production of said DKG is enhanced in the altered *Pantoea* host cell compared to the production of DKG in an unaltered *Pantoea* host cell cultured under essentially the same culture conditions. In one embodiment the invention relates to the altered *Pantoea* cell obtained according to the above method. In further embodiments, the method comprises a *Pantoea* cell genetically engineered to include a non-functional glucokinase gene and/or a non-functional gluconokinase gene.

In yet another aspect, the invention provides a method for increasing the availability of gluconate for oxidative pathway production of an ascorbic acid (ASA) intermediate which comprises obtaining an altered bacterial host cell, wherein an endogenous gluconate transporter gene has been rendered non-functional; culturing the altered bacterial host cell under suitable culture conditions in the presence of a carbon source to allow the production of an ASA intermediate; and obtaining the ASA intermediate, wherein the ASA intermediate is selected from the group consisting of 2-keto-D-gluconate (2-KDG), 2,5-diketo-D-gluconate (2,5-DKG), 2-keto-L-gulonic acid (2-KLG), 5-keto-D-gluconate (5-KDG) and L-idonic acid (IA) and the endogenous gluconate transporter gene encodes a gluconate transporter having the amino acid sequence of SEQ ID NO: 2, SEQ ID NO: 4 or a sequence having at least 80% identity to either SEQ ID NO: 2 or SEQ ID NO: 4.

Figure 2:
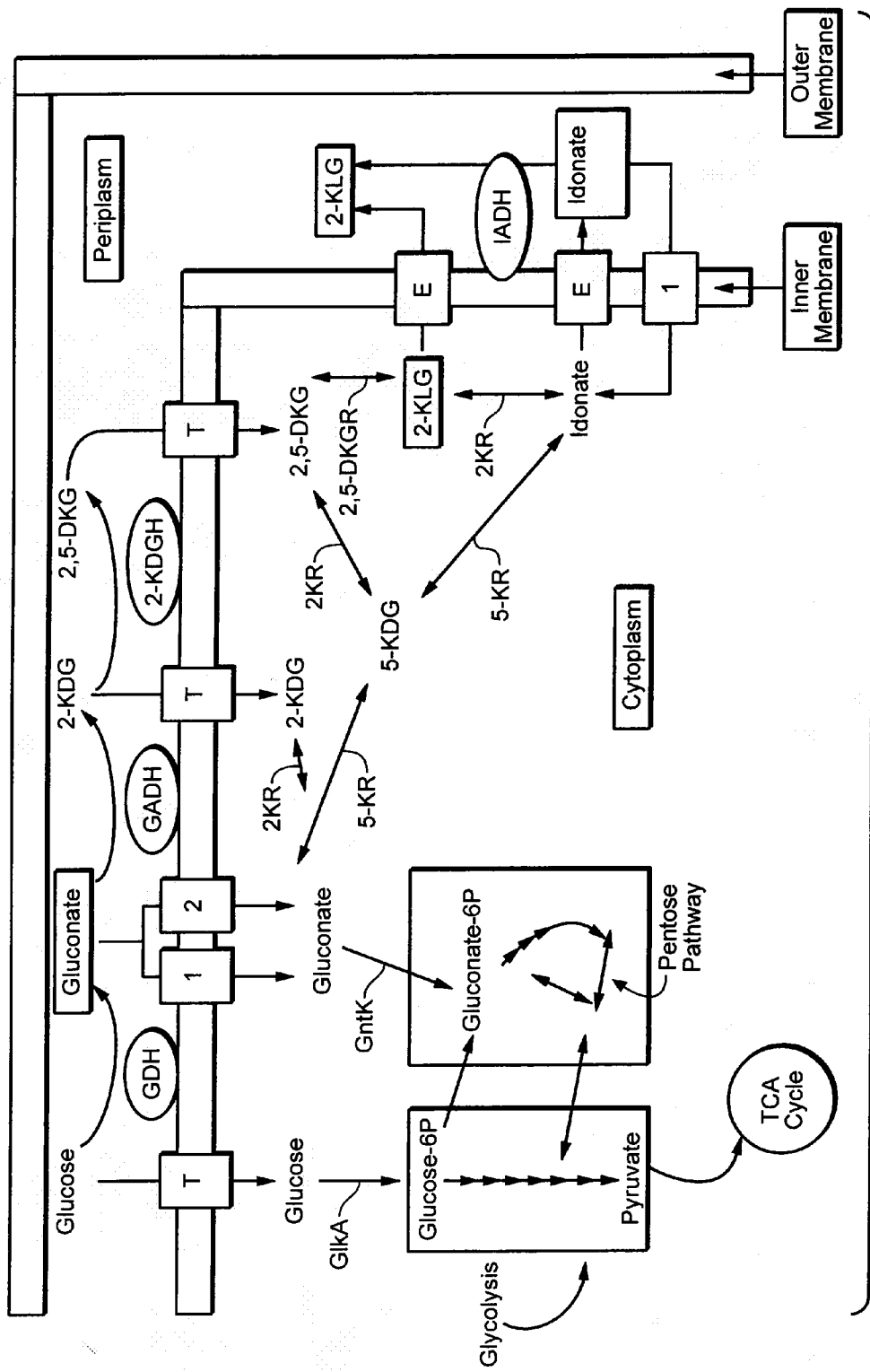
FIG. 2 provides a schematic representation of some of the metabolic routes involved in glucose assimilation in a bacterial host cell such as *Pantoea citrea*. The following abbreviations have been used in the figure and are applied throughout the disclosure: glucose dehydrogenase=(GDH); gluconic acid dehydrogenase=(GADH); 2-keto-D-gluconate=(2-KDG or KDG); 2-keto-D-gluconic acid dehydrogenase=(2-KDGH or KDGH); 2,5-diketogluconate=(2,5-DKG or DKG); 2,5-diketo-D-gluconic acid reductase=(2, 5 DKGR); 2-keto-L-gulonic acid=(2-KLG or KLG); 2-ketoreductase= (2KR or KR); 5-ketoreductase=(5KR or KR); 5-keto-D-gluconate=(5-KDG); idonate dehydrogenase =(IADH); glucokinase=(GIkA or Glk) and gluconokinase=(GntK). Boxes labeled with a "T" represent putative transporters and boxes labeled with an "E" represent putative efflux systems. Boxes labeled with a "1" or "2" represent putative gluconate transporters according to the invention.

As observed in FIG. 2, in a microbial cell there are multiple connections between oxidative and catabolic pathways, such as the glycolytic pathway, the pentose pathway, the tricarboxylic acid (TCA) cycle pathway and ASA intermediate production pathway. As can be seen, the inactivation of a gluconate transporter (1) and (2) blocks entry of gluconate into the cytoplasm resulting in a decrease in the amount of gluconate available for phosphorylation by GntK in the pentose assimilation pathway and resulting in a decrease in the amount of gluconate available for enzymatic reduction by 5-KR or 2-KR in the cytoplasm. Further it can be seen that inactivation of a gluconate transporter (1) also blocks entry of idonate into the cytoplasm and hence results in more substrate being made available for production of ASA intermediates such as KLG.

FIG. 3 depicts a nucleic acid sequence (SEQ ID NO: 1) for a *Pantoea citrea* gluconate transporter gene (gntU).

FIG. 4 depicts an amino acid sequence (SEQ ID NO: 2) for a *Pantoea citrea* gluconate transporter protein (GntU).

FIG. 5 depicts a nucleic acid sequence (SEQ ID NO: 3) for a *Pantoea citrea* gluconate transport gene (idnT).

FIG. 6 depicts an amino acid sequence (SEQ ID NO:4) for a *Pantoea citrea* gluconate transporter protein (IdnT).

Figure 7:
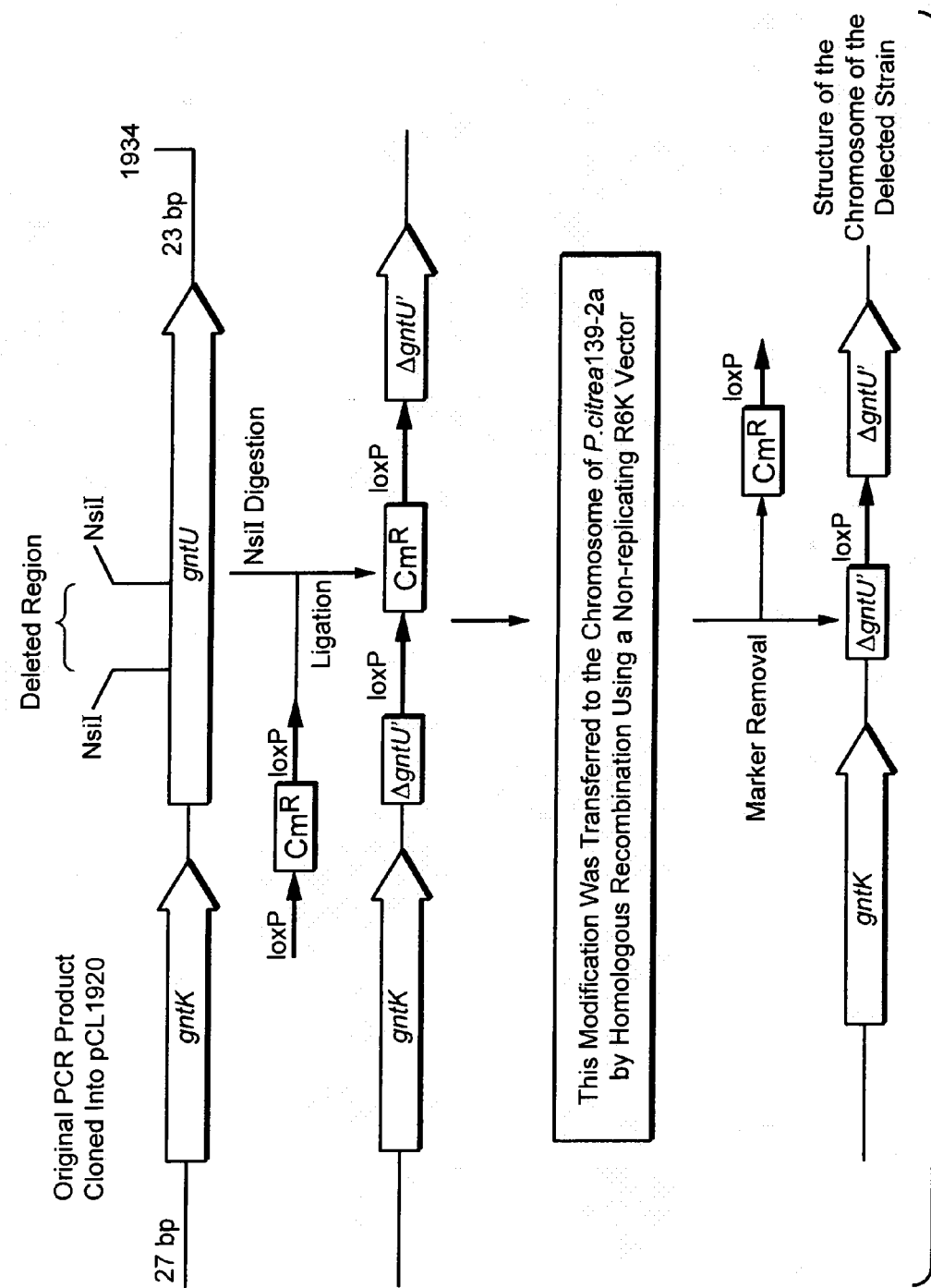

FIG. 7 is a general schematic illustrating the process and vectors used to inactivate a chromosomal gluconate transporter gene in a strain of *Pantoea citrea* by homologous recombination using a non-replicating R6K vector, wherein gntU is the gene encoding a gluconate transporter protein, gntK is the gene coding for glucokinase, NsiI is a restriction site, loxP is a recombinase recognition sequence and $Cm^R$ is the gene for the selective marker chloramphenicol. Reference is also made to example 1.

Figure 8:
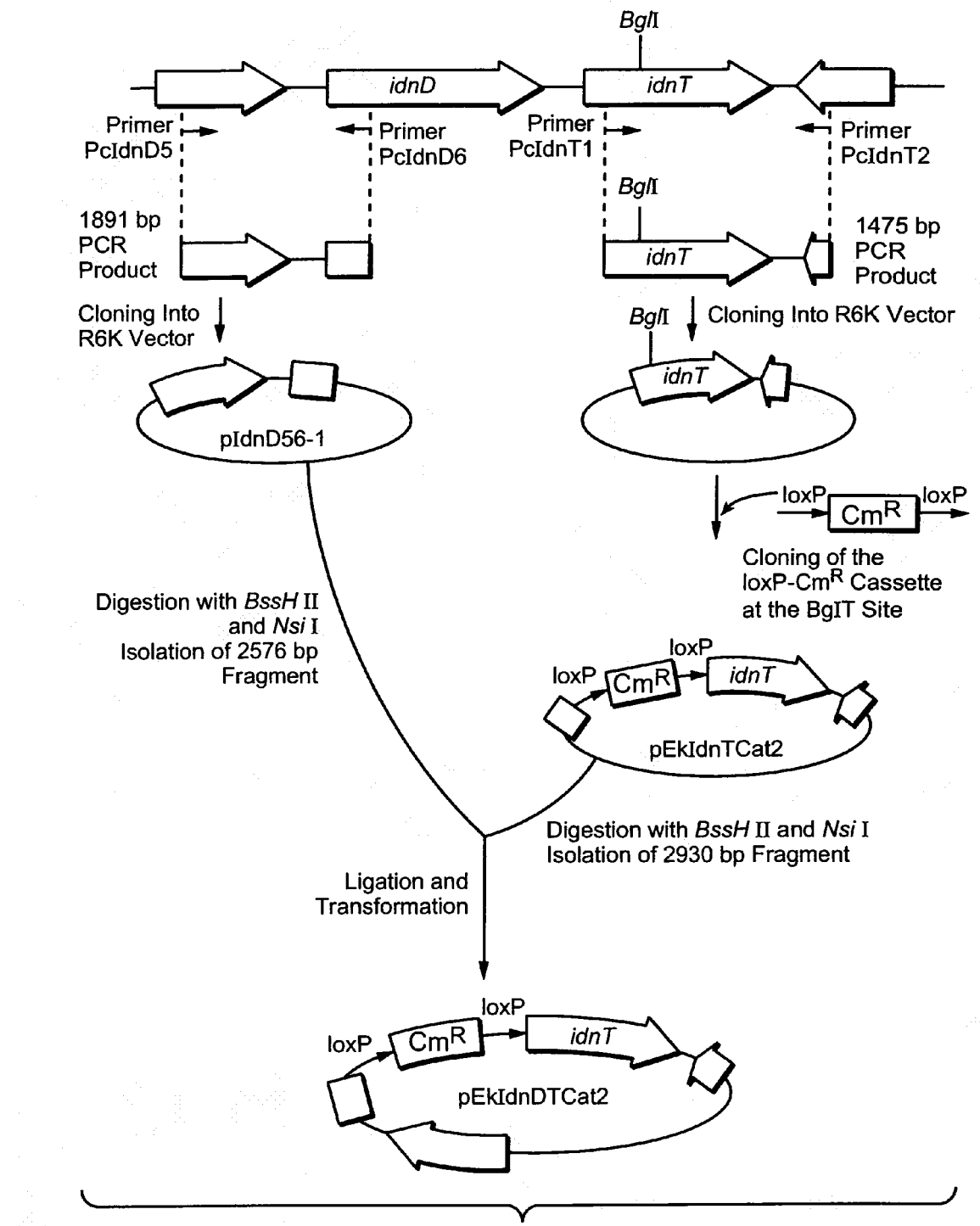

FIG. 8 is a general schematic illustrating the process and vectors used to inactivate a gluconate transporter chromosomal gene in a strain of *Pantoea citrea* by homologous recombination using a non-replicating R6K vector, wherein idnD is the gene coding for idonate dehydrogenase, idnT is the gene encoding a gluconate transporter protein, NsiI and BglI are restriction sites, loxP is a recombinase recognition sequence and $Cm^R$ is the gene for the selective marker chloramphenicol. The plasmid, pEkIdnDTcat2 was used for the transformation of the *Pantoea* host cell. Reference is also made to example 2.

Figures 9, 10:
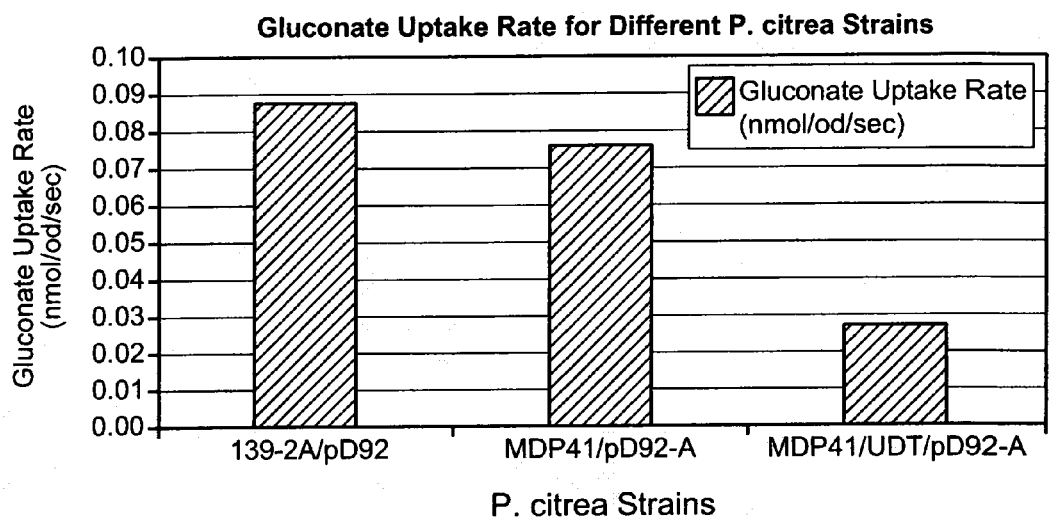

FIG. 9 depicts the results from gluconate uptake rate experiments (nmole/OD/sec) for three different *P. citrea* strains. Strain 139-2A/pD92 was used as a control and was derived from ATCC® Accession No. 39140. Strain MDP41/pD92-A was derived from 139-2A/pD92 and includes an interruption of glkA. Strain MDP41UDT/pD92-A was derived from MDP41/pD92-A (according to the teachings of examples 1 and 2) and includes, in addition to an interruption of glkA, a gntU deletion and an idnT deletion.

FIG. 10 depicts the percent sequence identity between 10 gluconate transporters. The amino acid sequence as set forth in SEQ ID NO: 2 is designated Pc-gntU. The percent identity between Pc-gntU and the other gluconate transporters is 34% or less. The amino acid sequence as set forth in SEQ ID NO: 4 is designated Pc-idnT. The percent identity between Pc-idnT and the other gluconate transporters is 76.3% or less. The percent amino acid sequence identity between SEQ ID NO: 2 and SEQ ID NO: 4 is 33%. Gluconate transports Ec-yjhF, Ec-dsdX, Ec-gntP, Ec-gntT, Ec-gntU, Ec-idnT and Ec-0454 are obtained from *E. coli* and Bs-gntP is obtained from *Bacillus*.

Figure 11:
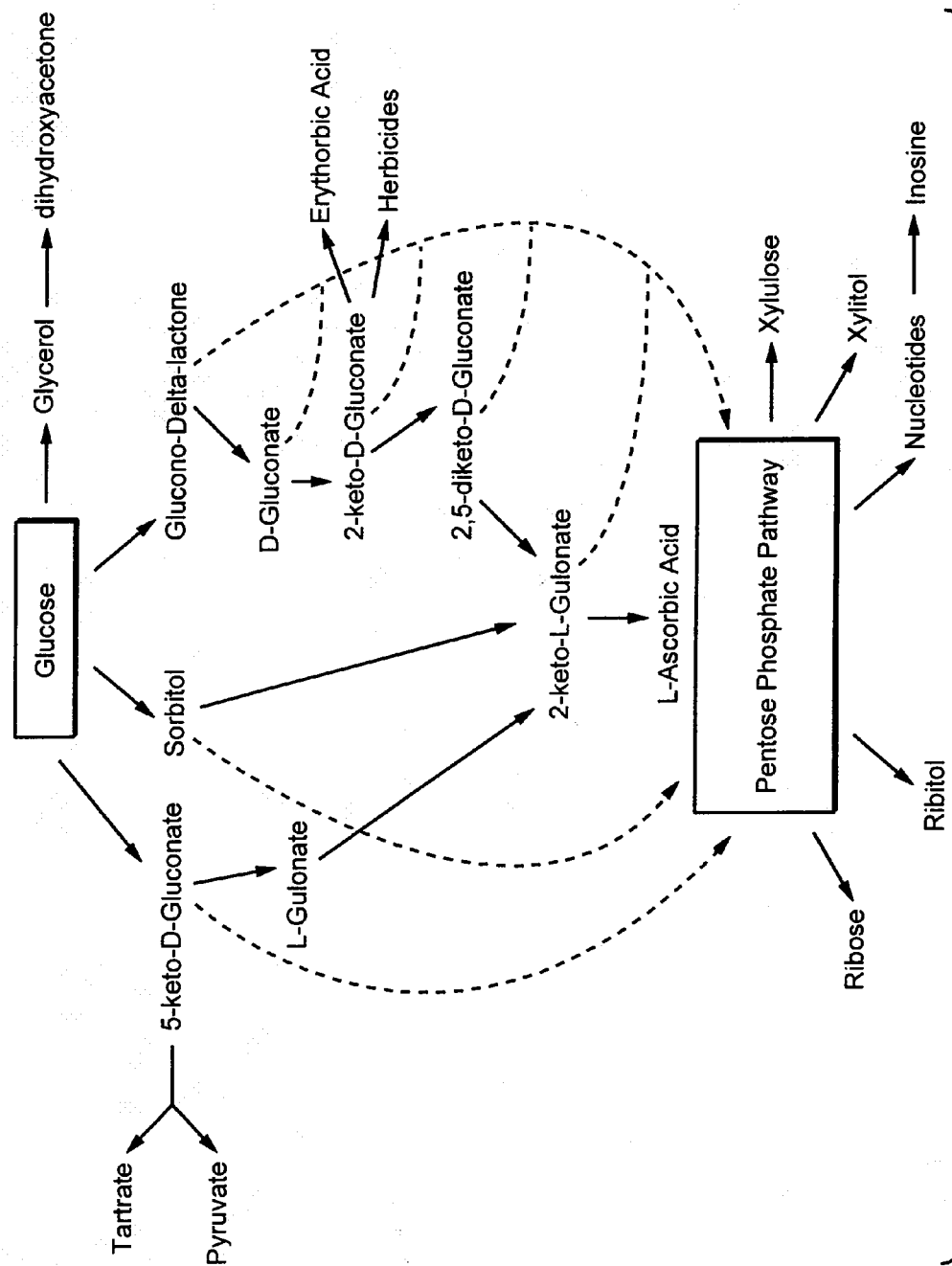

FIG. 11 generally depicts some of the metabolic pathways involved in the synthesis of various polyols that are of commercial relevance.

DETAILED DESCRIPTION OF THE INVENTION

Recombinant bacterial host cells have been constructed which produce polyols, particularly keto-polyols and more particularly ASA intermediates, and which are altered to reduce carbon substrate diverted to catabolic pathways. Possible catabolic routes which can be used to divert glucose into cellular metabolism involving at least one enzymatic step, include but are not limited to the formation of each of the following: glucose-6-P, fructose, sorbitol, gluconate-6-P, idonate, sorbosone, deoxy-gluconate, 2,5-di-keto-gluconate, and 2-keto-D-gluconate, 5-keto-D-gluconate and 2-keto-3-deoxygluconate. (See FIGS. 1 and 2).

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, MOLECULAR CLONING: A LABORATORY MANUAL, second edition (Sambrook et al., 1989) Cold Spring Harbor Laboratory Press; CURRENT PROTOCOLS IN MOLECULAR BIOLOGY (F. M. Ausubel et al., eds., 1987 and annual updates); OLIGONUCLEOTIDE SYNTHESIS (M. J. Gait, ed., 1984); PCR: THE POLYMERASE CHAIN REACTION, (Mullis et al., eds., 1994); and MANUAL OF INDUSTRIAL MICROBIOLOGY AND BIOTECHNOLOGY, Second Edition (A. L. Demain, et al., eds. 1999).

DEFINITIONS

Unless defined otherwise herein, all technical terms and scientific terms used herein have the same meaning as commonly understood by one of ordinary skill in the art to which this invention pertains. Singleton, et al., DICTIONARY OF MICROBIOLOGY AND MOLECULAR BIOLOGY, 2D ED., John Wiley and Sons, New York (1994) and Hale and Marham, THE HARPER DICTIONARY OF BIOLOGY, Harper Perennial, New York (1991) provide one of skill with general dictionaries of many of the terms used in this invention.

As used herein the term "polyol" means an alcohol molecule with numerous hydroxyl groups. A "keto-poly derivative" is a polyol which includes one or more keto groups in the polyol molecule. Examples of polyols include but are not limited to glucose, fructose, mannose, idose, galactose, sorbose, ribose, altose, arabinose, erythrose, xylose, xylulose, maltose, sucrose, erythrulose, gluconate, idonate, gulonate, galacturonate, mannitol, sorbitol, sorbosone, glycerol, erythritol, arabitol, DKG, KDG, KLG, gluconolactone and maltitol. The compounds may occur in either the D or L configuration.

As used herein an "ascorbic acid (ASA) intermediate" means a biochemical capable of being converted to ASA by enzymatic or chemical means and includes, but is not limited to, gluconate (GA); 2-keto-D-gluconate (2-KDG or KDG); 2,5-diketo-D-gluconate (2,5-DKG or DKG); 2-keto-L-gulonic acid (2KLG or KLG); 5-keto-D-gluconate (5-KDG) and L-idonic acid (IA).

As used herein, the term "carbon source" encompasses suitable carbon substrates ordinarily used by microorganisms, such as 6 carbon sugars, including but not limited to glucose (G), gulose, sorbose, fructose, idose, galactose and mannose all in either D or L form, or a combination of 6 carbon sugars, such as glucose and fructose, and/or 6 carbon sugar acids including but not limited to 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid or the enzymatic derivatives thereof.

As used herein, the phrase "transport system" refers to at least one macromolecule, such as a protein, which is located in a cell membrane and is involved in the translocation of a chemical compound, such as a carbon substrate, across a cell membrane and into or out from a cell or cellular compartment. A transport system may include two, three, four, five, six or more macromolecules, such as proteins. These proteins may or may not be simultaneously induced by a substrate. (Reference is made to Saier M. et al., (1998) in ADVANCES IN MICROBIAL PHYSIOLOGY (Poole R. K. ed) pages 81-136, Academic Press, San Diego, Calif. for a discussion of the classification of transporters). In the literature, a transporter system is sometimes referred to as a permease. For example, the gluconate permease (GntP) family in *E. coli* is encoded by seven transporter genes which include gntP, gntT, gntU, gntW, ORFf449, dsdX and ORFo454 (Peekhaus et al., (1997) *FEMS Micro. Lett.* 147:233-238). Reference is also made to Yamada et al., (1996) *Biosci. Biotech. Biochem.*, 60:1548-1550 and Tsunedomi et al., (2003) *J. Bacteriol.* 185:1783-1795. In one embodiment, a transporter protein as used herein is a "symporter". A symporter is defined as a transporter that transports two or more substrates or species together in the same direction in a coupled process using an electrochemical potential gradient. One example of a symporter is a proton coupled substrate transporter.

The term "gluconate transporter" as used herein refers to a protein that catalyzes the transport of gluconate into the cytoplasm across the internal cell membrane. In addition to gluconate, a gluconate transporter may catalyze the transport of other sugar acid molecules or sugar-keto acids across a cell membrane.

A "sugar acid molecule" is defined as a sugar molecule having one or more acid groups. Preferred sugar acids that may be transported by a gluconate transporter according to the invention will not only include gluconate, but may also include idonic acid, galacturonic acid, glucuronic acid and/or gulonic acid.

A "sugar-keto acid" is defined as a sugar molecule having one or more keto groups and one or more acid groups. A gluconate transporter according to the invention may also catalyze the transport of sugar keto acids, such as 2-keto-D-gluconic acid (2-KDG or KDG), 2-keto-L-gulonic acid (KLG), 5-keto-D-gluconic acid (5-KDG), D-tagaturonic acid and/or D-fructuroinc acid.

The term "KDG transporter" as used herein refers to a protein that catalyzes the transport of KDG across a cell membrane. More specifically the KDG transporter facilitates the entry of KDG into the cytoplasm across the internal cell membrane.

The term "glucose transporter" as used herein refers to a protein that catalyzes the transport of glucose across a cell membrane. More specifically the glucose transporter facilitates the entry of glucose into the cytoplasm across the internal cell membrane.

The term "DKG transporter" as used herein refers to a protein that catalyzes the transport of DKG across a cell membrane. More specifically the DKG transporter facilitates the entry of DKG into the cytoplasm across the internal cell membrane.

"Cytoplasm" or "cytoplasmic" refers to being within the inner cell membrane. Extracellular or outside the inner cell membrane refers to cell locations on the opposite side of a membrane from the cytoplasm, including but not limited to the periplasm. Internal or inner membrane (and sometimes referred to as the periplasmic membrane) refers to the barrier that separates the cytoplasm from the periplasm. Intracellular refers to the portion of the cell on the side of the membrane that is closest to the cytosol. Intracellular includes cystolic.

As used herein the term "gene" means a DNA segment that is involved in producing a polypeptide and includes regions preceding and following the coding regions as well as intervening sequences (introns) between individual coding segments (exons). As used herein when describing proteins and genes that encode them, the term for the gene is not capitalized and is italics, i.e. glkA. The term for the protein is generally not italicized and the first letter is capitalized, i.e. GlkA.

The terms "protein" and "polypeptide" are used interchangeability herein.

As used herein "oxidative pathway" of a host cell means that a host cell comprises at least one enzyme that oxidizes a carbon source, such as D-glucose and/or its metabolites. An oxidative pathway in a host cell may comprise, one, two, three or more enzymes. An example of an oxidative pathway is the formation of gluconate from glucose through the activity of glucose dehydrogenase. Another example of an oxidative pathway is the formation of DKG from glucose through the activity of glucose dehydrogenase, gluconate dehydrogenase and 2-KDG dehydrogenase.

Figure 1:
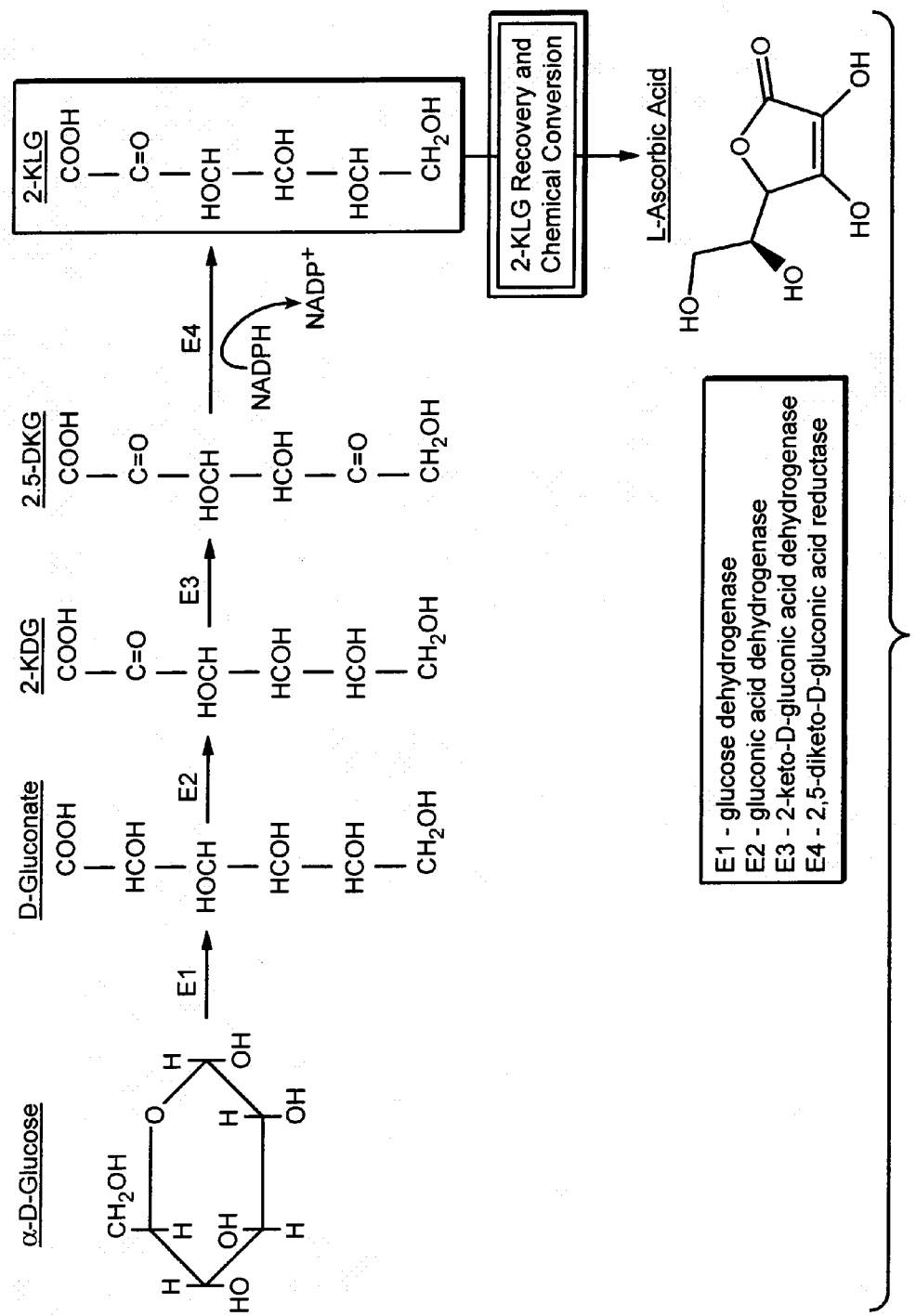
FIG. 1 depicts the oxidative pathway for the production of ascorbic acid (ASA). E1 stands for glucose dehydrogenase (GDH); E2 stands for gluconic acid dehydrogenase (GADH); E3 stands for 2-keto-D-gluconic acid dehydrogenase (KDGH); and E4 stands for 2,5-diketo-D-gluconic acid reductase (2,5 DKGR).

As used herein "catabolic pathway" of a host cell means that a host cell comprises at least one enzyme that generates at least one metabolic intermediate. Very often, the formation of the metabolic intermediate is coupled to the generation of ATP, NADPH, or NADH for example by phosphorylating a carbon source such as D-glucose and/or its metabolites. An intracellular catabolic pathway in a host cell means the host cell comprises the activity of at least one enzyme in the host cell cytosol. In some embodiments, a catabolic pathway comprises the activity of two, three or more enzymes. Catabolic pathways include but are not limited to glycolysis, the pentose pathway and the TCA cycle pathway (FIGS. 1 and 2).

As used herein, the phrase "glucokinase" (E.C.-2.7.1.2) means an enzyme which phosphorylates D-glucose or L-glucose at its 6th carbon. As used herein, the phrase "gluconokinase" (E.C.-2.7.1.12) means an enzyme which phosphorylates D-gluconate or L-gluconate at its $6^{th}$ carbon.

The term "nonfunctional", "inactivated" or "inactivation" when referring to a gene or a protein means that the known normal function or activity of the gene or protein has been eliminated or highly diminished. For example, inactivation of a gluconate transporter can be effected by inactivating the gntU and/or idnT chromosomal genes. Inactivation which renders the gene or protein non-functional includes such methods as deletions, mutations, substitutions, interruptions or insertions in the nucleic acid gene sequence.

A "deletion" of a gene as used herein may include deletion of the entire coding sequence, deletion of part of the coding sequence, deletion of the regulatory region, deletion of the translational signals or deletion of the coding sequence including flanking regions.

As used herein the term "mutation" when referring to a nucleic acid refers to any alteration in a nucleic acid such that the product of that nucleic acid is partially or totally inactivated. Examples of mutations include but are not limited to point mutations, frame shift mutations and deletions of part or all of a gene encoding a transporter.

As used herein, the term "modified" when referring to nucleic acid or a polynucleotide means that the nucleic acid has been altered in some way as compared to a wild type nucleic acid, such as by mutation in; deletion of part or all of the nucleic acid; or by being operably linked to a transcriptional control region.

An "altered bacterial host cell or strain" according to the invention is a bacterial cell having an inactivated gluconate transporter. In one embodiment, an altered bacterial host cell will have an enhanced level of expression (production) over the level of production of the same desired product in a corresponding unaltered bacterial host grown under essentially the same growth conditions. In other embodiments, an altered host cell will have an enhanced level of availability of gluconate to be used by the host cell to produce ASA intermediates as compared to a corresponding unaltered bacterial host cell.

An "unaltered bacterial host cell or strain" is a bacterial cell, which genetically corresponds to an altered bacterial host cell or strain but wherein the endogenous gene encoding the gluconate transporter encompassed by the invention is not inactivated and remains functional.

The "enhanced level of production" refers to an increased yield of the desired end-product, or amount of substrate as compared to the yield from an unaltered bacterial host when cultured under essentially the same conditions. For example an increase of 2%, 5%, 10%, 15%, 20%, 30%, 40% or more over the yield of the unaltered bacterial host. Yield, may be expressed in numerous ways including as a weight % (gm product/gm substrate) or gm/L per unit of time. The enhanced level of production results from the inactivation of one or more chromosomal genes encoding a gluconate transporter according to the invention. In a first embodiment, the enhanced level of production results from the deletion of one or more chromosomal genes encoding a gluconate transporter. In a second embodiment, the enhanced level of production results from the insertional inactivation (interruption) of one or more chromosomal genes encoding a gluconate transporter.

As used herein "chromosomal integration" is a process whereby an introduced polynucleotide is incorporated into a host cell chromosome. The process preferably takes place by homologous recombination.

As used herein, "modifying" the level of protein or enzyme activity produced by a host cell refers to controlling the levels of protein or enzymatic activity produced during culturing, such that the levels are increased or decreased as desired.

"Under transcriptional control" or "transcriptionally controlled" are terms well understood in the art that indicate that transcription of a polynucleotide sequence, usually a DNA sequence, depends on its being operably linked to an element which contributes to the initiation of, or promotes, transcription. "Operably linked" refers to a juxtaposition wherein the elements are in an arrangement allowing them to function. "Under translational control" is a term well understood in the art that indicates a regulatory process that occurs after the messenger RNA has been formed. "Expression" includes transcription and/or translation. The term "overexpressed" means an increased number of copies of the same gene in a host cell genome.

"Allowing the production of an ASA intermediate from a carbon source, wherein the production of said ASA intermediate is enhanced compared to the production of the ASA intermediate in a corresponding unaltered bacterial host cell or strain" means contacting the carbon source, with an altered bacterial strain to produce the desired end-product. By altering a gluconate transporter according to the invention, an altered bacterial host can demonstrate enhanced desired end-product production.

The phrase "desired end-product" or "desired product" as used herein refers to a desired compound to which the carbon substrate is bioconverted into. The desired end-product may be the actual compound sought or an intermediate along another pathway. Exemplary desired products are gluconic acid, 2-keto-D-gluconate; 2,5-diketo-D-gluconate; erythorbic acid; 5-keto-D-gluconate; 2-keto-L-gulonate; tartaric acid; D-ribose; riboflavin; deoxy-ribonucleotides; ribonucleotides; sorbitol; glycerol; sorbose; dihydroxyacetone; aromatic amino acids; aromatic compounds, such as P-hydroxybenzoic acids, quinones, catechol, indole, indigo, gallic acid, pyrogallol, melanin, adipic acid, and P-aminobenzoic acid; pyridoxine and aspartame. Particularly preferred desired products are keto derivatives of sorbitol, keto derivatives of gluconate and keto derivatives of glycerol.

As used herein, the term "bacteria" refers to any group of microscopic organisms that are prokaryotic, i.e., that lack a membrane-bound nucleus and organelles. All bacteria are surrounded by a lipid membrane that regulates the flow of materials in and out of the cell. A rigid cell wall completely surrounds the bacterium and lies outside the membrane. There are many different types of bacteria, some of which include, but are not limited to *Bacillus, Streptomyces, Pseudomonas*, and strains within the families of Enterobacteriaceae.

As used herein, the family "Enterobacteriaceae" refers to bacterial strains having the general characteristics of being gram negative and being facultatively anaerobic. For the production of ASA intermediates, preferred Enterobacteriaceae strains are those that are able to produce 2,5-diketo-D-gluconic acid from D-glucose or carbon sources which can be converted to D-glucose by the strain. (Kageyama et al., *International J. Sys. Bacteriol.* 42:203 (1992)). Included in the family of Enterobacteriaceae are *Erwinia, Enterobacter, Gluconobacter, Klebsiella, Escherichia* and *Pantoea*. In the present invention, a preferred Enterobacteriaceae fermentation strain for the production of ASA intermediates is a *Pantoea* species. The genus *Pantoea* includes *P. agglomerans, P. dispersa, P. punctata, P. citrea, P. terrea, P. ananas* and *P. stewartii* and in particular, *Pantoea citrea. Pantoea citrea* can be obtained from ATCC® (Manassas, Va.) for example ATCC® No. 39140. *Pantoea citrea* has sometimes been referred to as *Erwinia herbicola* or *Acetobacter cerenius*. Thus, it is intended that the genus *Pantoea* include species that have been reclassified, including but not limited to *Erwinia herbicola* or *Acetobacter cerenius*.

As used herein the family "*Bacillus*" refers to rod-shaped bacterial strains having the general characteristics of being gram positive and capable of producing resistant endospores in the presence of oxygen. Examples of *Bacillus* include *B. subtilis, B. licheniformis, B. lentus, B. circulans, B. lautus, B. amyloliquefaciens, B. stearothermophilus, B. alkalophilus, B. coagulans, B. thuringiensis* and *B. brevis*.

As used herein, the term "recombinant" refers to a host cell that has a modification of its genome, e.g., as by the addition of nucleic acid not naturally occurring in the organism or by a modification of nucleic acid naturally occurring in the host cell.

The term "heterologous" as used herein refers to nucleic acid or amino acid sequences not naturally occurring in the host cell. As used herein, the term "endogenous" refers to a nucleic acid or encoded amino acid naturally occurring in the host.

The terms "isolated" or "purified" as used herein refer to an enzyme, nucleic acid, protein, peptide or co-factor that is removed from at least one component with which it is naturally associated. In the present invention, an isolated nucleic acid can include a vector comprising the nucleic acid.

As used herein, the term "vector" refers to a polynucleotide construct designed to introduce nucleic acids into one or more cell types. Vectors include cloning vectors, expression vectors, shuttle vectors, plasmids and the like.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components.

A polynucleotide or polypeptide having a certain percentage (for example, 40%, 50%, 60%, 70%, 80%, 85%, 90%, 93%, 95%, 97% or 99%) of "sequence identity" to another sequence means that, when aligned, that percentage of bases or amino acids are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2. Another sequence software program that could be used is the TFastA Data Searching Program available in the Sequence Analysis Software Package Version 6.0 (Genetic Computer Group, University of Wisconsin, Madison, Wis.).

It is well understood in the art that the acidic derivatives of saccharides, may exist in a variety of ionization states depending upon their surrounding media, if in solution, or out of solution from which they are prepared if in solid form. The use of a term, such as, for example, idonic acid, to designate such molecules is intended to include all ionization states of the organic molecule referred to. Thus, for example, "idonic acid", its cyclized form "idonolactone", and "idonate" refer to the same organic moiety, and are not intended to specify particular ionization states or chemical forms.

The term "culturing" as used herein refers to fermentative bioconversion of a carbon substrate to the desired end-product within a reactor vessel. Bioconversion means contacting a microorganism with a carbon substrate to convert the carbon substrate to the desired end-product.

As used herein "ATCC®" refers to American Type Culture Collection located in Manassas, Va. 20108 (ATCC®, www/atcc.org).

As used herein, the term "comprising" and its cognates are used in their inclusive sense; that is, equivalent to the term "including" and its corresponding cognates.

"A," "an" and "the" include plural references unless the context clearly dictates otherwise.

Preferred Embodiments

A. Genes, Proteins and Vectors

The present application concerns isolated nucleic acid molecules encoding gluconate transporter proteins. In one embodiment, an isolated polynucleotide which encodes a gluconate transporter has the nucleic acid sequence set forth in SEQ ID NO: 1 or a nucleic acid sequence having at least 40%, 45%, 50%, 55%, 60%, 65%, 70%, 75%, 80%, 85%, 90%, 93%, 95%, 97%, 98% and 99% sequence identity to the sequence of SEQ ID NO: 1. Preferably the isolated polynucleotide will have at least 40% sequence identity, at least 80% sequence identity or at least 95% sequence identity to the nucleic acid sequence set forth in SEQ ID NO: 1. Preferably the isolated polynucleotide is obtained from a *Pantoea* host cell.

In another embodiment, the isolated polynucleotide which encodes a gluconate transporter has the nucleic acid sequence set forth in SEQ ID NO: 3 or a nucleic acid sequence having at least 40%, 45%, 50%, 55%, 60%, 65%, 70%, 75%, 80%, 85%, 90%, 93%, 95%, 97%, 98% and 99% sequence identity to the sequence of SEQ ID NO: 3. Preferably, the isolated polynucleotide will have at least 40% sequence identity, at least 80% sequence identity, or at least 95% sequence identity to the nucleic acid sequence set forth in SEQ ID NO: 3. Preferably, the isolated polynucleotide is obtained from a *Pantoea* host cell.

An isolated polynucleotide according to the invention will encode a gluconate transporter protein having the amino acid sequence set forth in SEQ ID NO: 2 or a gluconate transporter protein having at least 40%, 45%, 50%, 55%, 60%, 65%, 70%, 75%, 80%, 85%, 90%, 93%, 95%, 97%, 98% and 99% sequence identity to the sequence of SEQ ID NO: 2. Preferably the isolated polynucleotide encodes a gluconate transporter protein having the sequence as set forth in SEQ ID NO: 2 or encodes a gluconate transporter protein having at least 40% sequence identity, at least 80% sequence identity or at least 95% sequence identity to SEQ ID NO: 2. The gluconate transporter protein having the amino acid sequence as set forth in SEQ ID NO: 2 is designated herein as GntU.

An isolated polynucleotide according to the invention may also encode a gluconate transporter protein having the amino acid sequence set forth in SEQ ID NO: 4 or a gluconate transporter protein having 40%, 45%, 50%, 55%, 60%, 65%, 70%, 75%, 80%, 85%, 90%, 93%, 95%, 97%, 98% and 99% sequence identity to the sequence of SEQ ID NO: 4. Preferably, the isolated polynucleotide encodes a gluconate transporter protein having the sequence as set forth in SEQ ID NO: 4 or encodes a transporter protein having at least 80% sequence identity or at least 95% sequence identity to SEQ ID NO: 4. The protein having the amino acid sequence as set forth in SEQ ID NO: 4 is designated herein as IdnT. Additionally, in one embodiment this gluconate transporter and those having at least 80% sequence identity thereto are also able to facilitate the transport of idonate across the inner cellular membrane of a host bacterial cell.

One of skill in the art is well aware of the degeneracy of the genetic code and that an amino acid may be coded for by more than one codon. These variations are include as part of the invention herein.

A further embodiment of the invention includes an isolated gluconate transporter protein comprising the amino acid sequence set forth in SEQ ID NO: 2 or an amino acid sequence having at least 40%, 45%, 50%, 55%, 60%, 65%, 70%, 75%, 80%, 85%, 90%, 93%, 95%, 97%, 98% and 99% sequence identity to the sequence of SEQ ID NO: 2. In one embodiment, the gluconate transporter will have the amino acid sequence set forth in SEQ ID NO: 2 or at least 40%, at least 80% or at least 95% sequence identity thereof. The gluconate transporter protein set forth in SEQ ID NO: 2 was obtained from *Pantoea*. In another embodiment, the invention includes an isolated gluconate transporter protein comprising the amino acid sequence set forth in SEQ ID NO: 4 or an amino acid sequence having at least 40%, 45%, 50%, 55%, 60%, 65%, 70%, 75%, 80%, 85%, 90%, 93%, 95%, 97%, 98% and 99% sequence identity to the sequence of SEQ ID NO: 4. In one embodiment, the gluconate transporter will have the amino acid sequence set forth in SEQ ID NO: 4 or at least 80% sequence thereto. In this embodiment the gluconate transporter will also facilitate the transport of idonate. The gluconate transporter protein set forth in SEQ ID NO: 4 was obtained from *Pantoea*. In one embodiment, a preferred gluconate transporter is a transporter obtained from bacterial strains of *Pantoea*, particularly a strain of *P. citrea* or *P. agglomerans*.

A gluconate transporter according to the invention will catalyze the transport of gluconate but also may catalyze the transport of the sugar-keto acids, KDG, KLG, 5-KDG, D-Tagaturonic acid, and D-Fructuronic acid. Further a gluconate transporter according to the invention may also catalyze the transport of other sugar acids, such as idonic acid, galacturonic acid, gulonic acid and/or glucuronic acid.

Gluconate transporters according to the invention are members of the GntP family of transporters. Over 100 gluconate transporter proteins from various microorganisms have been identified. These microorganisms include *Escherichia, Bacillus, Haemophilus, Pseudomonas* and *Clostridium*. (Reference is made to Yamada et al., (1996) *Biosci. Biotech. Biochem.* 60:1548-1550; Bausch et al., (1998) *J. Bacteriol.* 180:3701-3710; Reizer et al., (1991) *Mol. Microbiol.* 5:1081-1089 and Peekhaus et al., (1997) *FEMS Microbiol. Lett.* 147: 233-238). The overall identity of some of the disclosed gluconate transporter proteins with the amino acid sequence illustrated in SEQ ID NO: 2 is less than about 34% identity and for SEQ ID NO: 4 less than about 76.3% identity (FIG. 10).

Naturally occurring gluconate transporter proteins have about 12 to 14 transmembrane domains and typically are about 400 to 450 amino acids in length. In this embodiment, a preferred isolated gluconate transporter is a protein obtained from bacterial strains of *Pantoea*, particularly a strain of *P. citrea* or *P. agglomerans*.

Methods useful for identifying gluconate transporter proteins found in bacterial microorganisms such as *Pantoea* species are well known in the art and would include hybridization studies. Thus, for example, nucleic acid sequences which hybridize under high stringency conditions to a gluconate transporter gene identified in FIGS. 4 and 6 or a complement thereof, may also encode proteins that function as a gluconate transporter. Hybridization includes the process by which a strand of nucleic acid joins with a complementary strand through base pairing. High stringency conditions are known in the art and see for example, Maniatis, et al., MOLECULAR CLONING: A LABORATORY MANUAL, 2d Edition (1989) and SHORT PROTOCOLS IN MOLECULAR BIOLOGY, ed Ausubel et al. Stringent conditions are sequence dependent and will be different in different circumstances. Longer sequences hybridize specifically at higher temperatures. An extensive guide to the hybridization of nucleic acids is found in Tijssen, TECHNIQUES IN BIOCHEMISTRY AND MOLECULAR BIOLOGY—HYBRIDIZATION WITH NUCLEIC ACID PROBES, Overview of Principles of Hybridization and the Strategy of Nucleic Acid Assays (1993). Generally stringent conditions are selected to be about 5 to 10 degrees lower than the thermal melting point Tm for the specific sequence at a defined ionic strength and pH. The Tm is the temperature (under defined ionic strength, pH and nucleic acid concentration) at which 50% of the probes complementary to the target, hybridize to the target sequence at equilibrium. Stringent conditions will be those in which the salt concentration is less than about 1.0 M sodium ion, typically about 0.01 to 1.0M sodium ion concentration (or other salts) at pH 7.0 to 8.3 and the temperature is at least 30° C. for short probes (e.g. for 10 to 50 nucleotides) and at least about 60° C. for long probes (e.g. greater than 50 nucleotide). Stringent conditions may also be achieved with the addition of destabilizing agents such as formamide. In another embodiment, less stringent hybridization conditions are used. For example moderate or low stringent conditions may be used.

PCR may also be used to screen for homologous sequences of gluconate transporters and reference is made to Chen et al., (1995) *Biotechniques* 18(4):609-612. Exemplary probe oligonucleotides that may be used for detecting gluconate transporter molecules include the polynucleotides set forth in SEQ ID NO:1 or SEQ ID NO: 3 or fragments thereof. These fragments may include at least 15, 20, 25, 30, 35, 40, 45, 50, 60, 65, 70, 75, 80, 85, 90 or more contiguous nucleotides from the reference sequence of SEQ ID NO: 1 or SEQ ID NO: 3. Additionally, an oligonucleotide useful in the present invention may comprise a nucleotide sequence encoding a polypeptide having at least 5, 10, 15, 20, 25, 30 or more contiguous amino acid residues of either SEQ ID NO: 2 or SEQ ID NO: 4. Other methods include protein bioassay or immunoassay techniques which include membrane-based, solution-based, or chip-based technologies for the detection and/or quantification of the nucleic acid or protein.

Gluconate transporter activity can be determined by a variety of methods. For example, using gluconate uptake assays and detection of metabolic products of gluconate or idonate such as by using HPLC as described further in the examples.

Moreover, it is believed that within the cells of the same species or strain, more than one gluconate transporter protein may be involved in the transport of gluconate into the cytoplasm. In one example, a family of gluconate transporter proteins of which GntU and IdnT are members would comprise a gluconate transporter system in a *Pantoea* cell.

Transporter proteins function by moving substrates across a cellular membrane. As shown in FIG. 2, the function of a gluconate transporter is to facilitate transport of a substrate, such as gluconate into the cytoplasm where it is then made available for cellular metabolism. By reducing the transport of gluconate into the cytoplasm by rendering a gluconate transporter gene non-functional, more substrate will be available for oxidative production of keto-sugars and ASA intermediates and particularly for KLG bioproduction.

B. Bacterial Host Cells

Particularly preferred bacterial host cells according to the invention are Enterobacteriaceae cells and particularly *E. coli* and *Pantoea* cells. Particularly preferred *Pantoea* cells are *P. citrea* and *P. aggolmerans* (U.S. Pat. No. 5,032,514). *Bacillus* sp. may also serve as host cells.

In one embodiment, an altered bacterial cell of the invention comprises at least one non-functional endogenous gluconate transporter. In one example, the altered bacterial cell would include a non-functional gluconate transporter wherein the gluconate transporter in the corresponding unaltered bacterial cell was encoded by a polynucleotide encoding the amino acid sequence set forth in SEQ ID NO: 2 or a polynucleotide encoding a gluconate transporter having an amino acid sequence of at least 40%, 45%, 50%, 55%, 60%, 65%, 70%, 75%, 80%, 85%, 90%, 95%, 97%, 98% or 99% identity with the sequence of SEQ ID NO: 2. In a further embodiment, the gluconate transporter in the unaltered bacterial host cell will be encode by a polynucleotide having the nucleic acid sequence of at least 80%, 85%, 90%, 95%, 97%, 98% and 99% identity with the sequence of SEQ ID NO: 1.

In another example, the altered bacterial cell would include a non-functional gluconate transporter wherein the gluconate transporter in the corresponding unaltered bacterial cell was encoded by a polynucleotide encoding the amino acid sequence set forth in SEQ ID NO: 4 or a polynucleotide encoding a gluconate transporter having an amino acid sequence with at least 80%, 85%, 90%, 95%, 97%, 98% or 99% identity with the sequence of SEQ ID NO: 4. In a further embodiment, the gluconate transporter in the unaltered bacterial host cell will be encoded by a polynucleotide having the nucleic acid sequence of at least 40%, 45%, 50%, 55%, 60%, 65%, 70%, 75%, 80%, 85%, 90%, 95%, 97% and 99% identity with the sequence of SEQ ID NO: 3.

Altered bacterial cells according to the invention may include more than one non-functional gluconate transporter protein. Altered cells according to the invention may include two, three, four or more non-functional gluconate transporter proteins. In some embodiments, at least two gluconate transporter proteins are rendered non-functional. In one specific example, a gluconate transporter having at least 90% sequence identity with the sequence SEQ ID NO: 2 and a gluconate transporter having at least 90% sequence identity with the sequence of SEQ ID NO: 4 are rendered non-functional in a bacterial host cell. In a second specific example, a gluconate transporter having at least 95% sequence identity with the sequence SEQ ID NO: 2 and a gluconate transporter having at least 95% sequence identity with the sequence of SEQ ID NO: 4 are rendered non-functional in a bacterial host cell If a gluconate transporter is rendered non-functional, the transport of the substrate gluconate across the inner cell membrane will be substantially reduced and in some cases gluconate will not be transported across the inner cell membrane. The reduction of gluconate transport results in increased availability of the gluconate substrate in the oxidative pathway for use in production of ASA intermediates.

C. Methods for Rendering Gluconate Transporters Non-Functional

In general, methods of rendering chromosomal genes non-functional are well known and a number of these techniques may be used to inactivate a gluconate transporter molecule according to the invention. In an altered bacterial strain according to the invention, the inactivation of the gluconate transporter genes will preferably be a stable and non-reverting inactivation. Some of these methods include the integration of DNA into a host cell and reference is made to Balbas et al., (1996), *Gene*, 172:65-69 and LeBorge et al., (1998), *Gene*, 223:213-219.

One preferred method of inactivation is a deletion of the gene encoding the gluconate transporter. The deletion may be partial as long as the sequences left in the chromosome are too short for biological activity of the gene. One method of deleting a gluconate transporter gene according to the invention includes constructing a vector which includes homologous flanking regions of the transporter coding sequence of interest. The flanking regions may include from about 1 bp to about 500 bp at the 5' and 3' ends. The flanking region of the vector may be larger than 500 bp but will preferably not include other genes in the region of the gene to be deleted which would result in these genes being inactivated or deleted. The vector construct may be introduced into a host cell by, for example, transformation and then integrated into the host cell chromosome. The end result is that the introduced DNA causes the endogenous gluconate gene to be deleted.

In another embodiment, inactivation is by insertion. Insertional inactivation includes interruption of the chromosomal coding region. For example when gntU is the gene to be inactivated, a DNA construct will comprise a nucleic acid sequence having the gntU gene interrupted by a selective marker. The selective marker will be flanked on each side by sections of the gntU coding sequence. The DNA construct aligns with essentially identical sequences of the gntU gene in the host chromosome and in a double crossover event the gntU gene is inactivated by the insertion of the selective marker. A selectable marker refers to a gene capable of expression in the host microorganism which allows for ease of selection of those hosts containing the vector. Examples of such selectable markers include but are not limited to antibiotic resistant genes such as, erythromycin, kanamycin, chloramphenicol and tetracycline.

In another embodiment, inactivation is by insertion in a single crossover event with a plasmid as the vector. For example, a gluconate transporter chromosomal gene such as gntU is aligned with a plasmid comprising the gntU gene or part of the gene coding sequence and a selective marker. The selective marker may be located within the gene coding sequence or on a part of the plasmid separate from the gene. The vector may be integrated into the bacterial chromosome, and the gene is inactivated by the insertion of the vector in the coding sequence.

Inactivation may also occur by a mutation of the gene. Methods of mutating genes are well known in the art and include but are not limited to chemical mutagenesis, site-directed mutation, generation of random mutations, and gapped-duplex approaches. (U.S. Pat. No. 4,760,025; Moring et al., *Biotech.* 2:646 (1984); and Kramer et al., *Nucleic Acids Res.* 12:9441 (1984)). Chemical mutagenesis may include the use chemicals that affect nonreplicating DNA, such as $HNO_2$ and $NH_2OH$, as well as agents that affect replicating DNA, such as acridine dyes. Specific methods for creating mutants using radiation and chemical agents are well documented in the art. see, for example T. D. Brock in BIOTECHNOLOGY: A TEXTBOOK OF INDUSTRIAL MICROBIOLOGY, 2nd Ed. (1989) Sinauer Associates, Inc. Sunderland, Mass. After mutagenesis has occurred, mutants having the desired property may be selected by a variety of methods, such as random screening or selective isolation on a selective media.

In some embodiments, an expression vector is constructed which contains a multiple cloning site cassette which preferably comprises at least one restriction endonuclease site unique to the vector, to facilitate ease of nucleic acid manipulation. In a preferred embodiment, the vector also comprises one or more selectable markers. In another preferred embodiment, a gluconate transporter gene is deleted by homologous recombination.

For example, as shown in FIG. 7, an inactivation cassette is constructed by first cloning a DNA fragment containing the gluconate transporter gene, gntU into a vector. To inactivate the gntU gene, an antibiotic resistance gene (i.e. a chloramphenicol, $Cm^R$ gene) is cloned into a unique restriction site found in the gluconate transporter gene. The insertion of the antibiotic marker into the gntU gene interrupts its normal coding sequence. The inactivation cassette is transferred to the host cell chromosome by homologous recombination using a non-replication R6K vector like pGP704 (Miller et al. (1988) *J. Bacteriol.* 170:2575-2583). The transfer of the cassette into the host cell chromosome is selected by the inclusion of $Cm^R$ by the host cell. Once the inactivation of the gntU gene has been corroborated, the $Cm^R$ is removed from the gntU coding region leaving an interrupting spacer (which in this example includes a copy of a loxP site) in the coding region, inactivating the coding region. (Palmeros et al., (2000) *Gene* 247:255-264). A similar process is seen in FIG. 8 for inactivation of the endogenous idnT gene. However in this example two fragments, one including a loxP-$Cm^R$-idnT cassette and one including a idnD cassette are ligated together and transformed into the host resulting in both the interruption of the gluconate transporter, idnT and the gene idnD which encodes idonate dehydrogenase.

Plasmids which can be used as vectors in bacterial organisms are well known and reference is made to Maniatis, et al., MOLECULAR CLONING: A LABORATORY MANUAL, 2d Edition (1989) AND MOLECULAR CLONING: A LABORATORY MANUAL, second edition (Sambrook et al., 1989) and Bron, S, Chapter 3, Plasmids, in MOLECULAR BIOLOGY METHODS FOR BACILLUS, Ed. Harwood and Cutting, (1990) John Wiley & Sons Ltd.

A preferred plasmid for the recombinant introduction of polynucleotides encoding non-naturally occurring proteins or enzymes into a strain of Enterobacteriaceae is RSF1010, a mobilizable, but not self transmissible plasmid which has the capability to replicate in a broad range of bacterial hosts, including Gram– and Gram+bacteria. (Frey et al., 1989, *The Molecular Biology of IncQ Plasmids*. In: Thomas (Ed.), PROMISCUOUS PLASMIDS OF GRAM NEGATIVE BACTERIA. Academic Press, London, pp. 79-94). Frey et al. report on three regions found to affect the mobilization properties of RSF1010 (Frey et al. (1992) *Gene* 113:101-106).

In a further embodiment, the expression product of an inactivated or deleted gene may be a truncated protein as long as the protein has a change in its biological activity. The change in biological activity could be an altered activity, but preferably is loss of biological activity.

D. Additional Gene Modifications

In one embodiment, altered bacterial cells according to the invention may include further modifications of chromosomal genes. These modifications to a bacterial host cell may have been realized prior to, simultaneously with, or after inactivation of one or more gluconate transporter genes. The chromosomal modifications may include inactivations, such as deletions or interruptions of endogenous chromosomal genes, modifications resulting in increased expression of endogenous chromosomal genes, and inclusion of heterologous genes. More specific examples of modifications to altered host cells of the invention include but are not limited to:

(i) modifications concerning additional gluconate transporter genes;
(ii) modifications to genes encoding glucose transporters;
(iii) modifications to genes encoding KDG transporters;
(iv) modifications to genes encoding DKG transporters (DKG permease genes), such as prmA, prmB, PE6, PE1 and YiaX2 (See WO 02/12468; WO 02/12481 and WO 02/12528);
(v) gene modifications resulting in overexpression of certain genes, for example overexpression of DKG permease genes or aroZ genes, which encode dehydratases; and
(vi) modifications to a polynucleotide that uncouples the catabolic pathway from the oxidative pathway such as by inactivating an enzyme that phosphorylates D-glucose or D-gluconate at its 6th carbon and more specifically inactivating a hexokinase gene, a glucokinase gene or a gluconokinase gene i.e. gntK and/or glkA and reference is made to WO 02/081440.

In certain preferred embodiments, an altered bacterial strain according to the invention will include an inactivated gntK and/or an inactivated glkA gene. In another preferred embodiment, an altered bacterial strain according to the invention will include an overexpressed DKG permease.

In certain embodiments, the altered bacterial strain may embody two inactivated genes, three inactivated genes, four inactivated genes, five inactivated genes, six inactivated genes or more. The inactivated genes may be contiguous to one another or may be located in separate regions of the bacterial chromosome. An inactivated chromosomal gene may have a necessary function under certain conditions, but the gene is not necessary for bacterial strain viability under laboratory conditions. Preferred laboratory conditions include but are not limited to conditions such as growth in a fermentator, in a shake flask, in plate media or the like.

In some embodiments, the altered bacterial host cells are recombinant *Pantoea* cells which comprise a first inactivated endogenous gluconate transporter gene, which prior to inactivation encoded a gluconate transporter having at least 80%, 90%, and 95% sequence identity with SEQ ID NO: 2, a second inactivated endogenous gluconate transporter gene, which prior to inactivation encoded a gluconate transporter having at least 80%, 90% and 95% sequence identity with SEQ ID NO; 4, and an inactivated endogenous glucokinase gene. In some embodiments, the inactivated gluconate transporter genes will have been deleted from the altered host cell.

In another embodiment, the host cell may be genetically engineered to include genes encoding enzymes known to effect the conversion of glucose or other ordinary metabolites to 2,5-DKG or 2-KLG from the organisms known to contain them. Examples of the enzymes effecting the conversion of an ordinary metabolite to 2,5-DKG or 2-KLG are D-glucose dehydrogenase (Adachi, O. et al., (1980) *Agric. Biol. Chem.*, 44:301-308; Ameyama, M. et al., (1981) *Agric. Biol. Chem.* 45:851-861; Smith et al. (1989) *Biochem. J.* 261:973; and Neijssel et al., (1989) *Antonie Van Leauvenhoek* 56(1):51-61); D-gluconate dehydrogenase (McIntire, W. et al., (1985) *Biochem. J.*, 231:651-654; Shinagawa, E. et al., (1976) *Agric. Biol. Chem.* 40:475-483; Shinagawa, E. et al., (1978) *Agric. Biol. Chem.* 42:1055-1057; and Matsushita et al. (1979), *J. Biochem.* 85:1173); 5-keto-D-gluconate dehydrogenase and 2-keto-D-gluconate dehydrogenase (Shinagawa, E. et al., (1981) *Agric. Biol. Chem.*, 45:1079-1085 and Stroshane (1977) *Biotechnol. BioEng.* 19(4) 459); and 2,5-diketo-D-gluconic acid reductase (U.S. Pat. Nos. 5,795,761; 5,376,544; 5,583,025; 4,757,012; 4,758,514; 5,008,193; 5,004,690; and 5,032,514).

A preferred altered bacterial strain according to the invention will be an *E. coli*, *Bacillus* or *Pantoea* strain and particularly a *Pantoea* strain such as a *P. citrea*. Preferably, the altered bacterial strain will comprise an inactivated endogenous gluconate transporter gene and one or more of the following: a) an inactivated endogenous glucokinase gene; b) an inactivated endogenous gluconokinase gene; c) an inactivated endogenous glycerol kinase gene; d) an over-expressed DKG transporter gene and e) an inactivated or disrupted glucose transport system, such as the phosphoenolpyruvate glucose phosphotransferase system (PTS).

In one embodiment when KLG is the desired intermediate, nucleic acid encoding 2,5 DKG reductase (DKGR) is recombinantly introduced into the bacterial fermentation strain. Many species have been found to contain DKGR particularly members of the Coryneform group, including the genera *Corynebacterium*, *Brevibacterium*, and *Arthrobacter*. In a further embodiment DKGR from *Corynebacterium* sp. strain SHS752001 (Grindley et al., 1988, *Applied and Environmental Microbiology* 54: 1770-1775) is recombinantly introduced into a host strain, such as a *Pantoea* host strain. Production of recombinant 2,5 DKG reductase by *Erwinia herbicola* is disclosed in U.S. Pat. No. 5,008,193.

Gene transfer techniques for bacterial cells are well known and these techniques include transformation, transduction, conjugation and protoplast fusion. Gene transfer is the process of transferring a gene or polynucleotide to a cell or cells wherein exogenously added DNA is taken up by a bacterium. General transformation procedures are taught in CURRENT PROTOCOLS IN MOLECULAR BIOLOGY (vol. 1, edited by Ausubel et al., John Wiley & Sons, Inc. 1987, Chapter 9) and include calcium phosphate methods, transformation using DEAE-Dextran and electroporation. A variety of transformation procedures are known by those of skill in the art for introducing nucleic acids in a given host cell. (Reference is also made to U.S. Pat. No. 5,032,514; Potter H. (1988) *Anal. Biochem* 174:361-373; Sambrook, J. et al., MOLECULAR CLONING: A LABORATORY MANUAL, Cold Spring Harbor Laboratory Press (1989); and Ferrari et al., Genetics, pgs 57-72 in BACILLUS, Harwood et al., Eds. Plenum Publishing Corp).

Transformation of a host cell can be detected by the presence/absence of marker gene expression which can suggest whether the nucleic acid of interest is present. However, its expression should be confirmed. For example, if the nucleic acid encoding a gluconate transporter is inserted within a marker gene sequence, recombinant cells containing the insert can be identified by the absence of marker gene function. Alternatively, a marker gene can be placed in tandem with nucleic acid encoding the transporter under the control of a single promoter. Expression of the marker gene in response to induction or selection usually indicates expression of the protein or enzyme as well. Once a bacterial microorganism capable of carrying out the conversion as described above has been created, the process of the invention may be carried out in a variety of ways depending on the nature of the construction of the expression vectors for the recombinant proteins and upon the growth characteristics of the host.

E. Cell Cultures and Fermentations

Methods suitable for the maintenance and growth of bacterial cells is well known and reference is made to the MANUAL OF METHODS OF GENERAL BACTERIOLOGY, Eds. P. Gerhardt et al., American Society for Microbiology, Washington D.C. (1981) and T. D. Brock in BIOTECHNOLOGY: A TEXTBOOK OF INDUSTRIAL MICROBIOLOGY, 2nd ed. (1989) Sinauer Associates, Sunderland, Mass.

Cell Precultures—Typically cell cultures are grown at 25 to 32° C., and preferably about 28 or 29° C. in appropriate media. Exemplary growth media useful in the present invention are common commercially prepared media such as but not limited to Luria Bertani (LB) broth, Sabouraud Dextrose (SD) broth or Yeast medium (YM) broth. These may be obtained from for example, GIBCO/BRL (Gaithersburg, Md.). Other defined or synthetic growth media may be used and the appropriate medium for growth of the particular bacterial microorganism will be known by one skilled in the art of microbiology or fermentation science. Suitable pH ranges preferred for the fermentation are between pH 5 to pH 8. Preferred ranges for seed flasks are pH 7 to pH 7.5 and preferred ranges for the reactor vessels are pH 5 to pH 6. It will be appreciated by one of skill in the art of fermentation microbiology that a number of factors affecting the fermentation processes may have to be optimized and controlled in order to maximize the ascorbic acid intermediate production. Many of these factors such as pH, carbon source concentration, and dissolved oxygen levels may affect enzymatic processes depending on the cell types used for ascorbic acid intermediate production.

The production of ASA intermediates can proceed in a fermentative environment, that is, in an in vivo environment, or a non-fermentative environment, that is, in an in vitro environment; or combined in vivo/in vitro environments. The fermentation or bioreactor may be performed in a batch process, a Fed-batch process or in a continuous process.

In Vivo Biocatalytic Environment

Biocatalysis begins with culturing an altered host cell according to the invention in an environment with a suitable carbon source ordinarily used by Enterobacteriaceae or other bacterial strains. Suitable carbon sources include 6 carbon sugars, for example, glucose, or a 6 carbon sugar acid, or combinations of 6 carbon sugars and/or 6 carbon sugar acids. Other carbon sources include, but are not limited to galactose, lactose, fructose, or the enzymatic derivatives of such.

In addition, fermentation media must contain suitable carbon substrates which will include but are not limited to monosaccharides such as glucose, oligosaccharides such as lactose or sucrose, polysaccharides such as starch or cellulose and unpurified mixtures from a renewable feedstocks such as cheese whey permeate, cornsteep liquor, sugar beet molasses, and barley malt. Additionally, the carbon substrate may be one-carbon substrates such as carbon. While it is contemplated that the source of carbon utilized in the present invention may encompass a wide variety of carbon containing substrates and will only be limited by the choice of organism, the preferred carbon substrates include glucose, fructose and sucrose and mixtures thereof. By using mixtures of glucose and fructose in combination with the altered bacterial strains described herein, uncoupling of the oxidative pathways from the catabolic pathways allows the use of glucose for improved yield and conversion to the desired ASA intermediate while utilizing the fructose to satisfy the metabolic requirements of the host cells.

In one embodiment, the concentration of the carbon substrate in the seed solution is from about 55% to about 75% on a weight/weight basis. Preferably, the concentration is from about 60 to about 70% on a weight/weight basis. Most preferably the concentration used is 60% to 67% glucose.

In addition to an appropriate carbon source, fermentation media must contain suitable minerals, salts, vitamins, cofactors and buffers suitable for the growth or the cultures and promotion of the enzymatic pathway necessary for ascorbic acid intermediate production.

Batch, Fed-Batch and Continuous Fermentations

The present invention may employ a batch fermentation process, a modified batch fermentation process called Fed-batch or a continuous fermentation process.

A classical batch fermentation is a closed system where the composition of the media is set at the beginning of the fermentation and not subject to artificial alterations during the fermentation. At the beginning of the fermentation the media is inoculated with the desired bacterial organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of desired end products or intermediates.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in T. D. Brock in BIOTECHNOLOGY: A TEXTBOOK OF INDUSTRIAL MICROBIOLOGY, Second Edition (1989) Sinauer Associates, Inc. Sunderland, Mass.

Continuous fermentation is an open system where a defined fermentation media is added continuously to a bioreactor and simultaneously an equal amount of conditioned media is removed for processing. Continuous fermentation generally maintains the cultures at a constant high density where cells are primarily in log phase growth. Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

In one illustrative in vivo example of a pathway in *Pantoea*, D-glucose undergoes a series of membrane oxidative steps through enzymatic conversions, which may include the enzymes D-glucose dehydrogenase, D-gluconate dehydrogenase and 2-keto-D-gluconate dehydrogenase to give intermediates which may include, but are not limited to GA, KDG, and DKG, see FIGS. 1 and 2. These intermediates undergo a series of intracellular reducing steps through enzymatic conversions, which may include the enzymes 2,5-diketo-D-gluconate reductase (DKGR),2-keto reductase (2-KR) and 5-keto reductase (5-KR) to give end products which include but are not limited to KLG and IA. In a preferred embodiment of the in vivo environment for the production of ASA intermediates, gluconate is not transported across the host cell membrane which results in an increased availability of gluconate for oxidative pathway production of ASA intermediates.

F. Recovery, Identification and Purification of ASA Intermediates

Methods for detection of ASA intermediates, ASA and ASA stereoisomers such as D-araboascorbic acid (erythorbic acid), L-araboascorbic acid, and D-xyloascorbic acid include the use of redox-titration with 2,6 dichloroindophenol (Burton et al. (1979) *J. Assoc. Pub. Analysts* 17:105) or other suitable reagents; high-performance liquid chromatography (HPLC) using anion exchange; and electro-redox procedures (Pachia, (1976) *Anal. Chem.* 48:364). The skilled artisan will be well aware of controls to be applied in utilizing these detection methods. Alternatively, the intermediates can also be formulated directly from the fermentation broth or bioreactor and granulated or put in a liquid formulation. KLG produced by a process of the present invention may be further converted to ascorbic acid and the KDG to erythorbate by means known to those of skill in the art, see for example, Reichstein and Grussner, *Helv. Chim. Acta.*, 17, 311-328 (1934).

G. Increased Yield of Desired Products from the ASA Pathway

The catabolic pathway is uncoupled from the ASA oxidative pathway to increase the availability of gluconate or idonate for ASA intermediate production. As shown in FIGS. 1 and 2 gluconate can be transported across the inner cell membrane to the cytoplasm. Gluconate may then be phosphorylated, for example to gluconate—6-phosphate and made available for catabolic metabolism in the pentose pathway. Additionally, gluconate may be enzymatically reduced to 5-KDG or 2-KDG in the cytoplasm. Inactivation or modification of the levels of a gluconate transporter according to the invention by inactivation of the nucleic acid encoding the same, results in an increased amount of gluconate available for the oxidative ASA production pathway resulting in a desired product. Idonate may also be transported by the gluconate transporter across the inner membrane into the cytoplasm and through a series of enzymatic steps be converted to gluconate. This gluconate may then be phosphorylated as described above. Inactivation or modification of the levels of a gluconate transporter according to the invention by inactivation of the nucleic acid encoding the same, results in an increased amount of idonate available for conversion to 2-KLG. (FIGS. 1 and 2).

In an embodiment of the invention, the catabolic pathway is uncoupled from the ASA oxidative pathway to increase the production of KDG. Inactivation of the gluconate transporter diminishes the transport of gluconate across the inner cell membrane and reduces the availability of gluconate for phosphorylation by a kinase. Inactivation of the gluconate transporter gene or modification of the levels of the gluconate transporter results in the increased yield of a desired product, e.g. KDG.

In another embodiment, the catabolic pathway is uncoupled from the productive oxidative pathway to increase the production of DKG. Inactivation or modifying the levels of the gluconate transporter by modifying the nucleic acid or polypeptide encoding the same, results in the increased yield of the desired product, e.g. DKG.

In a further embodiment, the catabolic pathway is uncoupled from the productive oxidative pathway to increase the production of KLG. Inactivation or modifying the levels of the gluconate transporter by modifying the nucleic acid or polypeptide encoding the same, results in the increased yield of the desired product, e.g. KLG.

In another embodiment, the catabolic pathway is uncoupled from the productive pathway to increase the production of erythorbic acid. Inactivation or modifying the levels of the gluconate transporter by modifying the nucleic acid or polypeptide encoding the same, results in the increased yield of DKG which is an intermediate in the synthesis of erythorbic acid.

General Experimental Methods

Cells: All commercially available cells used in the following examples were obtained from the ATCC® and are identified in the text by their ATCC® number. Recombinant *P. citrea* cells used as a control were derived from ATCC 39140. (Also reference is made to Truesdell et al., (1991) *J. Bacteriol.* 173:6651-6656).

Materials and Methods suitable for the maintenance and growth of bacterial cultures were found in MANUAL OF METHODS FOR GENERAL BACTERIOLOGY (Phillipp Gerhardt, R. G. E. Murray, Ralph N. Costilow, Eugene W. Nester, Willis A. Wood, Noel R. Krieg and G. Briggs Phillips, eds), pp. 210-213. American Society for Microbiology, Washington, D.C. or in Thomas D. Brock in BIOTECHNOLOGY: A TEXTBOOK OF INDUSTRIAL MICROBIOLOGY, Second Edition (1989) Sinauer Associates, Inc., Sunderland, Mass. All reagents and materials used for the growth of bacterial cells were obtained from Diffco Laboratories (Detroit, Mich.), Aldrich Chemicals (Milwaukee, Wis.) or Sigma Chemical Company (St. Louis, Mo.) unless otherwise specified.

Ascorbic acid intermediate analysis: The presence of ascorbic acid intermediates, e.g., 2-KLG, was verified by running a HPLC analysis. Fermentation reactor vessel samples were drawn off the tank and loaded onto Dionex (Sunnyvale, Calif., Product No. 043118) Ion Pac AS10 column (4 mm times 250 mm) connected to a Waters 2690 Separation Module and a Waters 410 Differential Refractometer (Milford, Mass.).

The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXAMPLES

Example 1

Inactivation of the gntU ORF Encoding a Gluconate Transporter in *P. citrea*

Cloning of the gntKU Operon

A 1934-bp DNA fragment containing the gntK and gntU structural genes from *Pantoea citrea* was amplified by PCR with GntKUF1 (SEQ ID NO: 5) plus GntKUR1 (SEQ ID NO: 6) primer pairs using standard techniques (Sambrook et al., MOLECULAR CLONING: A LABORATORY MANUAL, Cold Spring Harbor Laboratory Press (1989) 2nd Ed.). In addition to the structural genes, the PCR fragment carries 27 bp upstream of the gntK gene and 23 bp downstream of the gntU (FIG. 7). This PCR product was cloned into the HindIII site of pCL1920 vector resulting in plasmid pCL-GntKU2 (6489-bp) (Lerner et al., (1990) *Nucleic Acids Res.* 18:4631). This was constructed into E. coli TOP10 strain (Invitrogen, Carlsbad, Calif.) and checked by EcoRI and PstI restriction enzymes for correct insert and orientation.

Construction of the plasmid used to inactivate gntU: In general, the strategy used to inactivate genes by homologous recombination with a vector has been delineated before and reference is made to Miller et al., (1988) *J. Bacteriol.* 170: 2575-2583. This general approach was used to inactivate gntU.

The pCL-GntKU2 plasmid described above was used for inactivation of the chromosomal gntU. pCL-GntKU2 was digested with NsiI enzyme (Roche Applied Science) to remove the 435-bp region from the middle of the gntUgene. A cat-loxP, 1080-bp cassette (Palmeros et al., (2000) *Gene* 247: 255-264) was inserted into the construct resulting in plasmid pCLKUCat1 (7131-bp). The orientation of the cat-loxP cassette was checked with Scal1+SpeI restriction enzymes. The 2580-bp gntKU+cat-loxP region was amplified by PCR using primers GntKUF1 (SEQ ID NO: 5) and GntKUR1 (SEQ ID NO: 6), and ligated with the 502-bp DNA fragment that contains the minimal R6K origin of replication (ori). This particular DNA was obtained by PCR using plasmid pGP704 (Miller et al., (1988) J. Bacteriol. 170:2575-2583) as PCR substrate with primers

```
R6K1
(TGTCAGCCGTTAAGTGTTCCTGTG)     (SEQ ID NO. 18)
and

R6K2
(CAGTTCAACCTGTTGATAGTACG).     (SEQ ID NO. 19)
```

The ligation product was transformed into *E. coli* PIR1 strain (Invitrogen, Carlsbad, Calif.) to generate the plasmid pKU-CatR6-1 (3087-bp). This plasmid was used to inactivate the gntU gene. In this construct, a 650-bp and 850-bp region of homology is available at the 5'- and 3'-end of the gntU gene, respectively, for homologous recombination into the *P. citrea* chromosome. This recombination event should not, affect the proximal gntKgene in the gntKU operon.

Transformation into *P. citrea* strains: After checking pKUCatR6-1 with AatII+Accl restriction enzymes, the plasmid was used to transform the strain MDP41of *P. citrea*. All transformations were done by standard electroporation. (Sambrook et al., Molecular Cloning: A Laboratory Manual, Cold Spring Harbor Laboratory Press (1989) 2nd Ed.). Transformants were selected on LA+Cm12 plates (LA is LB plus agar+ plates with 12 ppm chloramphenicol (Cm). Hundreds of Cm-resistant (CmR) colonies appeared. Four colonies were checked by PCR analysis as described below.

Verification of the altered gntU strains: To distinguish between single and double crossover events, the junction points were checked with one outside primer plus one cat gene specific primer. With GntKUF3 (outside) (SEQ ID NO: 7)+cat4 (SEQ ID NO: 11) and GntKUF4 (outside) (SEQ ID NO: 8)+cat4 (SEQ ID NO: 11) primer pairs, all four transformants amplified a 0.99-kb and a 0.95-kb fragment, respectively. With cat3 (SEQ ID NO: 10)+GntKUR3 (outside) (SEQ ID NO: 9), only No. 2 and No. 4 transformants amplified the expected 1.45-kb. Thus, No. 2 and No. 4 transformants had undergone a double cross-over event wherein the gntU was deleted. In contrast, No. 1 and No. 3 transformants had undergone a single cross-over event wherein the gntU remained intact at the gntU locus.

The 1.5-kb and 1.0-kb PCR products obtained with GntKUF4+cat4 (SEQ ID NO: 8+SEQ ID NO: 11) and cat3+GntKUR3 (SEQ ID NO: 10+SEQ ID NO: 9) primer pairs were digested with BglII and PstI enzymes, respectively, to verify the authenticity of the gntU deletion of these strains. Expected digestion patterns were obtained with both enzymes.

The No. 2 transformant was named MDP41U2 and further used in experiments.
Removal of the Chloramphenicol Marker (CmR) from MDP41U2.

The CmR marker from strain MDP41U2 was removed by bacteriophage P1Cre recombinase using the procedure disclosed in Palmeros et al. (2000) *Gene* 247:255-264. Briefly, plasmid pJW168 expressing the IPTG-inducible Cre recombinase was introduced into MDP41U2 strain by electroporation, The removal of CmR marker was achieved by screening colonies for chloramphenicol sensitivity (CmS) phenotype on antibiotic-free LA plates followed by PCR verification. Finally plasmid pJW168 was eliminated from the CmS strain by growing the strains at non-permissible temperature and checking for carbenicillin-sensitivity (CarbS) of the strains. The marker-less gntU deletion strain was named MDP41UF and was used for adding the idnT deletion.

TABLE 1

Primers used for gntU Deletion

| Name | Sequence (5' to 3') | SEQ ID NO. |
|---|---|---|
| GntKUF1 | TTGCTGCATCAACAGTCGGAG | 5 |
| GntKUR1 | GTTATTCCGGCACAAGCAGCC | 6 |
| GntKUF3 | GCGCTGGCCACGGTAGTTA | 7 |
| GntKUF4 | CGAAGAAGCCGCCAGGATGTTA | 8 |
| GntKUR3 | CCGGCGGTATTATTTTGTTTCTGA | 9 |
| Cat3 | GAAAGTTGGAACCTCTTACGTGCCG | 10 |
| Cat4 | ACAACAGTACTGCGATGAGTGGCAG | 11 |

Example 2

Inactivation of the idnT ORF Encoding a Gluconate Transporter in *Pantoea citrea*

Construction of the idnDT Deletion Plasmid:
Primers PcIdnT-1 (SEQ ID NO: 12) and PcIdnT-2 (SEQ ID NO: 13) were designed approximately 1 kb upstream and 1 kb downstream of the idnT gene (SEQ ID NO: 3). The amplification of PCR product of 1473-bp was obtained and cloned into pUniBluntV5-His-Topo (Echo Cloning System from Invitrogen). The resulting plasmid was transformed into *E. coli* PIR1 strain (Invitrogen, Carlsbad, Calif.) and appropriate restriction enzymes were used to check for the correct orientation of the gene.

IdnT gene was interrupted using BglI enzyme followed by insertion of a cat-loxP (1080-bp) cassette (Palmeros et al., (2000) Gene 247:255-264) resulting in plasmid pEkIdnT-Cat2 (4813-bp). As described in example 1, the orientation of the cat-loxP cassette was checked with appropriate restriction enzymes.

The following 2 primers PcIdnD5 (SEQ ID NO: 14)+ PcIdnD6 (SEQ ID NO: 15) were used to amplify the IdnD gene which is upstream of the idnT gene. A 1891-bp fragment encompassing the IdnD gene was amplified by PCR using known techniques and was cloned into pUniBluntV5-His-Topo (Echo Cloning Systems, Invitrogen) resulting in a plasmid called pIdnD56-1.

Construction of pEkIdnD56-1 and pEkIdnTCat2 to obtain the final plasmid pEkIdnDTCat2.

pEkIdnTCat2 was digested with BssH II and NsiI enzymes to remove a 1883-bp region of R6k on and partial Km resistance gene, and the remaining 2930-bp of IdnT gene with the cat-loxP cassette was purified and ligated to IdnD gene as follows:

pIdnD56-1 was digested with BssH II and NsiI enzymes and a 2576-bp fragment containing the IdnD gene with R6K on region was purified and ligated to 2930-bp of IdnT gene with the cat-loxP cassette followed by transformation into *E. coli* PIR1 strain to generate the final plasmid pEkIdnDT Cat2 (5506-bp) that was used for idnDT deletion. Plasmid pEkIdnDT Cat2 was verified with NcoI+Bgl II enzymes.
Transformation of pEkIdnDT Cat2 into *P. citrea* MDP41UF Strain.

The plasmid pEkIdnDTCat2 was transformed into *P. citrea* MDP41U2 strain using the same procedure as described above in example 1 and transformants were selected on LA+Cm12. Hundreds of CmR colonies were obtained followed by picking and patching simultaneously onto LA+Cm12 and LA+Kan50 plates to screen for kanamycin-sensitive (Kan$^S$) clones. Seven (Cm$^R$Kan$^S$) colonies were checked by PCR for the deletion of the idnDT region with appropriate primers as described herein and one colony was subsequently named MDP41UDT. (FIG. 8)
Verification of the idnDT Deletion in MDP41UDT:

A set of outside primers (PcIdnD7 (SEQ ID NO: 17)+ PcIdnT4 (SEQ ID NO: 16)) were used to verify the idnDT deletion. Another set of outside primers plus one cat gene specific primer (pcIdnD7 (SEQ ID NO: 19)+Cat4 (SEQ ID NO: 11)) & (PcIdnT4 (SEQ ID NO: 16)+Cat3 (SEQ ID NO: 10)) were used to verify the junctions of the deleted regions with the cat-loxP region.

Plasmid pD92-A (14.2-kb) was derived from plasmid pD92 (12.6-kb). pD92 was constructed by cloning the structural gene for the 2,5-diketo-D-gluconate reductase B from *Corynebacterium* sp. (Grindley et al., (1988) *Appl. Environ. Microbiol.* 54:1770-1775) into pI43 (U.S. Pat. No. 5,008, 193). The structural gene for permA gene described in WO 02/12468, WO 02/12528 and WO 02/12481 was introduced into the unique NotI site of plasmid pD92. This site is located in the structural gene of the streptomycin resistant (Strep$^R$) gene and the cloning of permA caused its inactivation. In plasmid pD92-A, the expression of permA gene is driven by its native promoter. Plasmid pD92-A was then transformed into MDP41UDT strain, resulting in MDP41UDT/pD92-A.

TABLE 2

Primers used for IdnT gene deletion

| Name | Sequence 5' to 3' | SEQ ID NO. |
|---|---|---|
| PcIdnT-1 | TAGGTATAGCCGAAGGGATGACAC | SEQ ID NO. 12 |
| PcIdnT-2 | AGAGCCTTTGCCTTTGATAACAGC | SEQ ID NO. 13 |
| PcIdnD5 | CTTTGGCCGCTGAACTGACGAGAT | SEQ ID NO. 14 |
| PcIdnD6 | TATAAACAGAAAAGGACAGATGAG | SEQ ID NO. 15 |
| PcIdnT-4 | TACCAGCCGCATACCGATACACC | SEQ ID NO. 16 |
| PcIdnD7 | CCGGTTATTCGCGTTATGTG | SEQ ID NO. 17 |
| Cat3 | GAAAGTTGGAACCTCTTACGTGCCG | SEQ ID NO. 10 |
| Cat4 | ACAACAGTACTGCGATGAGTGGCAG | SEQ ID NO. 11 |

Example 3

Shake Flask Experiments

Three strains of *Pantoea citrea* were used in this example:
(1) Strain 139-2A/pD92 was used as a control.
(2) Strain MDP41/pD92A disclosed in WO 02/081440 which includes an interruption in glkA.
(3) Strain MDP41UDT/pD92-A (as described above in examples 1 and 2) which includes an interruption in glkA and a deletion in gntU and idnT.

These strains were grown in the following medium ($KH_2PO_4$ (12.0 g/L); $K_2HPO_4$ (4.0 g/L); $MgSO_4.7H_2O$ (2.0 g/L); Difco Soytone (2.0 g/L); Sodium citrate (0.1 g/L); Fructose (5.0 g/L); $(NH_4)_2SO_4$ (1.0 g/L); Nicotinic acid (0.02 g/L); $FeCl_3.6H_2O$ (5 mL/L of a 0.4 g/L stock solution) and Trace salts (5 mL/L—of the following solution: 0.58 g/L $ZnSO_4.7H_2O$, 0.34 g/L $MnSO_4.H_2O$, 0.48 g/L $Na_2MoO_4.2H_2O$) with fructose as the sole carbon source or with a mixed carbon source (fructose, gluconate and DKG) in the range from 0.1% to 1.0%. Cells were grown at a temperature between 20-37° C., (preferably below 30° C.) and at a pH 7.0 (but a pH range of 5.0 to 8.0 should also work).

Gluconate uptake biochemical assay: —Samples of the fermentation broth containing cells of the strains designated above were withdrawn from the respective shake flasks and were quenched on ice-water bath. The fermentation broth was centrifuged at refrigerating conditions and the supernatant discarded. The cell pellet was washes with 0.95% ice cold saline solution followed by two washed with gluconate uptake assay buffer (100 mM ice-cold potassium phosphate, pH 6.9 containing 10 mM fructose). Cells were suspended in the same assay buffer to an optical density of 12 at 550 nm, and then were incubated at room temperature and preferably 28° C. The gluconate uptake assay was started by mixing the cell suspension solution with $C^{14}$ enriched radio-isotoped gluconate. The time course of gluconate uptake was performed using vacuum/filter based quenching using ice-cold gluconate uptake assay buffer. Gluconate uptake measurements were done by radioisotope incorporation in the cells and the data obtained plotted against time to give the gluconate uptake rate. (See FIG. 9).

The results support that deletion of gntU and idnT were effective in lowering the gluconate uptake rate. In this experiment, the rate of gluconate uptake rate for the control (139-2A/pD92) and the strain MDP41/pD92-A were similar. The gluconate uptake rate of MDP41UDT/pD92-A which includes the interruption of glkA, deletion of gntU and deletion of idnT further reduced gluconate uptake rate by 70% compared to the control.

Example 4

Fermentor Experiments with *Pantoea citrea* Host Cells having a Deletion of gntU and idnT Seed Train: A vial of culture containing the indicated strains which was stored in liquid nitrogen, was thawed in air and 0.75 mL was added to a sterile 2-L Erlenmeyer flasks containing 500 mL of seed medium. Flasks were incubated at 29° C. and 250 rpm for 12 hours. Transfer criteria is an $OD_{550}$ greater than 2.5.

Seed flask medium—A medium composition was made according to the following: $KH_2PO_4$ (12.0 g/L); $K_2HPO_4$ (4.0 g/L); $MgSO4.7H_2O$ (2.0 g/L); Difco Soytone (2.0 g/L); Sodium citrate (0.1 g/L); Fructose (5.0 g/L); $(NH_4)_2SO_4$ (1.0 g/L); Nicotinic acid (0.02 g/L); $FeCl_3.6H_2O$ (5 mL/L of a 0.4 g/L stock solution) and Trace salts (5 mL/L—of the following solution: 0.58 g/L $ZnSO_4.7H_2O$, 0.34 g/L $MnSO_4.H_2O$, 0.48 g/L $Na_2MoO_4.2H_2O$).

The pH of the medium solution was adjusted to 7.0±0.1 unit with 20% NaOH. Tetracycline HCl was added to a final concentration of 20 mg/L (2 mL/L of a 10 g/L stock solution). The resulting medium solution was then filter sterilized with a 0.2µ filter unit. The sterile medium was added to a previously autoclaved flask.

Production Fermentor—Additions to the reactor vessel prior to sterilization included: $KH_2PO_4$ (3.5 g/L); $MgSO_4.7H_2O$ (1.0 g/L); $(NH_4)_2SO_4$ (0.92 g/L); Mono-sodium glutamate (15.0 g/L); $ZnSO_4.7H_2O$ (5.79 mg/L); $MnSO_4.H_2O$ (3.44 mg/L); $Na_2MoO_4.2H_2O$ (4.70 mg/L); $FeCl_3.6H_2O$ (2.20 mg/L); Choline chloride (0.112 g/L) and Mazu DF-204 (0.167 g/L) an antifoaming agent.

The above constituted media was sterilized at 121° C. for 45 minutes. After tank sterilization, the following additions were made to the fermentation tank: Nicotinic acid (16.8 mg/L); Ca-pantothenate (3.36 mg/L); Glucose (25 g/L) and Fructose (25 g/L).

The final volume after sterilization and addition of post-sterilization components was 6.0 L. The so prepared tank and medium were inoculated with the full entire contents from seed flasks prepared as described to give a volume of 6.5 L.

Growth conditions were at 29° C. and pH 6.0. Agitation rate, back pressure, and air flow are adjusted as needed to keep dissolved oxygen above zero. When the sugars initially batched into the medium have been exhausted, a fed-batch process as previously described herein is employed. In this example both glucose and fructose are used as substrates in contrast to the standard fed-batch process where one substrate is employed.

As observed in Table 3 below, the yield of KLG obtained in MDP41UDT/pD92-A was greater than the yield obtained in the control MDP41/pD92-A.

TABLE 3

Fermentation Yield

| | Performance Metrics for Yield on KLG on Sugars | | | | |
|---|---|---|---|---|---|
| Strain | Average Yield (g/g) | Standard Deviation | Maximum | Minimum | Number |
| MDP41/pD92-A | 0.601 | 0.021 | 0.636 | 0.581 | 8 |
| MDP41UDT/ pD92-A | 0.643 | 0.009 | 0.654 | 0.630 | 5 |
| t-test | 0.001 | | | | |

MDP41/pD92-A is the control strain and includes a glkA interruption. Strain MDP41UDT/pD92-A is derived from MDP41/pD92 and includes a glkA interruption, a gntU deletion and an idnT deletion.

A further unexpected result included the increased production of KLG in relation to the formation of IA. KLG was measured as described above in the general experimental methods. Typically KLG is reduced further within strains to produce idonic acid. After fermentation is complete, air can be circulated through the fermentor and a membrane bound dehydrogenase oxidizes the IA back to KLG. With the deletion of gntU and idnT, the ratio of KLG to IA is increased thus reducing the time required for the back conversion of IA to KLG (Table 4). Reference is also made to FIG. 2.

TABLE 4

Ratio of KLG to IA

| STRAIN | KLG (G/L) | IA (G/L) | RATIO |
|---|---|---|---|
| MDP41/PD92-A | 189 | 75 | 2.52 |
| MDP41UDT/PD92-A | 214 | 47 | 4.55 |

The invention claimed is:

1. An altered Enterobacteriaceae strain comprising an inactivated endogenous gluconate transporter protein, wherein the inactivated endogenous gluconate transporter protein has at least 95% sequence identity with the amino acid sequence of SEQ ID NO: 2, or the amino acid sequence of SEQ ID NO: 4.

2. The altered Enterobacteriaceae strain of claim 1, comprising a further inactivated endogenous gluconate transporter protein.

3. The altered Enterobacteriaceae strain of claim 1, wherein the inactivated endogenous gluconate transporter proteins is rendered nonfunctional by deletion of the gene encoding the endogenous gluconate transporter protein.

4. The altered Enterobacteriaceae strain of claim 1, wherein said Enterobacteriaceae strain is selected from the group of *Pantoea, Gluconobacter, Erwinia, Klebsiella*, and *Escherichia* strains.

5. The altered Enterobacteriaceae strain of claim 4 further comprising an inactivated endogenous glucokinase gene.

6. A recombinant *Pantoea* strain comprising
   a) a first inactivated endogenous gluconate transporter gene, wherein the first gluconate transporter gene prior to inactivation encoded a gluconate transporter having at least 90% sequence identity with SEQ ID NO: 2,
   b) a second inactivated endogenous gluconate transporter gene, wherein the second gluconate transporter gene prior to inactivation encoded a gluconate transporter having at least 90% sequence identity with SEQ ID NO: 4, and
   c) an inactivated endogenous glucokinase gene.

7. The recombinant *Pantoea* strain of claim 6, wherein the first inactivated endogenous gluconate transporter gene and the second inactivated endogenous gluconate transporter gene have been deleted.

* * * * *

SEQUENCE LISTING

<160> NUMBER OF SEQ ID NOS: 19

<210> SEQ ID NO 1
<211> LENGTH: 1341
<212> TYPE: DNA
<213> ORGANISM: Pantoea citrea

<400> SEQUENCE: 1

```
atgataagta ccgcaacact ggtgctaacc gcagccggat cagttctgct gctgttactg      60
ctggttatga agccaggat gcatgctttt gtcgctttaa tgttagtctc cgtgggtgcc     120
gggatgatgt ccggaatgcc actgataaaa attactgaaa ccatgcaaaa aggcatgggt     180
ggcactcttg ctttctggc cattgtggtc gcactgggag ccatgttcgg aaaaattctg     240
catgaaaccg gggctgtcga tcagattgct atccgcatgc tgaaaacctt tggtgaaaaa     300
cgggcgcact atgcgatggg tattgccgga tttatctgtg cattgccgtt atttttgaa     360
gtggccattg tattgctgat aagcattgcg tttgctgttg ccagacgtac tggtggcaat     420
ctggtgaaac tggtgattcc gttgtttgcc ggggttgcgg cggcagcggc ttttgtactg     480
ccggggccag ctccaatgct actggcctcg cagatgcatg ctgattttgg ctggatgatc     540
ctgatagggt tatgtgcagc catccctggc atgttgattg ccggtccgtt gtttggcagc     600
tttatttccc gacatgttca cttttctctg cctgccgaag atactcagcc gcaagttgaa     660
gcccataagc tcccctcttt tggttttagc ctgtcactga tcctgttttcc gctggtgctg     720
gtagggctaa aaactatcgg cgcacatttt gtggctgccg gaactccggt atacaacttc     780
ctggagttta ttggtcatcc gtttattgcg attctgctgg cctgtctgat caccatctat     840
ggtctggcgt atcgtcaggg gatggataaa tcacggatta tgcagatctg cggggaagcg     900
ctacaacctg ccggtattat tctgctggtg attggtgcgg tgggggtatt taaacaggta     960
ctggtggatt ccggagtagg tccggcactg ggtgatgccg ttgcaggtgc cggattaccg    1020
gtggctgtgg cctgttttat cctggcgggt gctgtcagga tcattcaggg ttctgcgact    1080
gttgcctgtc tgacggcagt cggactgatt atgccgtgta cgaaccgtt gcattacagt    1140
ggtgctcagc tggctgcact ttctgtctgt attggcggtg gatcgattat tttcagccat    1200
gtgaatgacg ctggtttctg gttatttggt cgttttaccg gagcctcaga agccgaaaca    1260
ctgaagacct ggacgttgat ggaaactatt ctcggaacca gtggtggcat cattggcatg    1320
ctggccttct ggctgctgag c                                              1341
```

<210> SEQ ID NO 2
<211> LENGTH: 447
<212> TYPE: PRT
<213> ORGANISM: Pantoea citrea

<400> SEQUENCE: 2

```
Met Ile Ser Thr Ala Thr Leu Val Leu Thr Ala Ala Gly Ser Val Leu
  1               5                  10                  15

Leu Leu Leu Leu Val Met Lys Ala Arg Met His Ala Phe Val Ala
             20                  25                  30

Leu Met Leu Val Ser Val Gly Ala Gly Met Met Ser Gly Met Pro Leu
         35                  40                  45

Ile Lys Ile Thr Glu Thr Met Gln Lys Gly Met Gly Gly Thr Leu Gly
     50                  55                  60

Phe Leu Ala Ile Val Val Ala Leu Gly Ala Met Phe Gly Lys Ile Leu
 65                  70                  75                  80
```

```
His Glu Thr Gly Ala Val Asp Gln Ile Ala Ile Arg Met Leu Lys Thr
                85                  90                  95

Phe Gly Glu Lys Arg Ala His Tyr Ala Met Gly Ile Ala Gly Phe Ile
            100                 105                 110

Cys Ala Leu Pro Leu Phe Phe Glu Val Ala Ile Val Leu Leu Ile Ser
            115                 120                 125

Ile Ala Phe Ala Val Ala Arg Arg Thr Gly Gly Asn Leu Val Lys Leu
    130                 135                 140

Val Ile Pro Leu Phe Ala Gly Val Ala Ala Ala Ala Phe Val Leu
145                 150                 155                 160

Pro Gly Pro Ala Pro Met Leu Leu Ala Ser Gln Met His Ala Asp Phe
                165                 170                 175

Gly Trp Met Ile Leu Ile Gly Leu Cys Ala Ala Ile Pro Gly Met Leu
            180                 185                 190

Ile Ala Gly Pro Leu Phe Gly Ser Phe Ile Ser Arg His Val His Phe
            195                 200                 205

Ser Leu Pro Ala Glu Asp Thr Gln Pro Gln Val Glu Ala His Lys Leu
    210                 215                 220

Pro Ser Phe Gly Phe Ser Leu Ser Leu Ile Leu Phe Pro Leu Val Leu
225                 230                 235                 240

Val Gly Leu Lys Thr Ile Gly Ala His Phe Val Ala Ala Gly Thr Pro
                245                 250                 255

Val Tyr Asn Phe Leu Glu Phe Ile Gly His Pro Phe Ile Ala Ile Leu
            260                 265                 270

Leu Ala Cys Leu Ile Thr Ile Tyr Gly Leu Ala Tyr Arg Gln Gly Met
            275                 280                 285

Asp Lys Ser Arg Ile Met Gln Ile Cys Gly Glu Ala Leu Gln Pro Ala
    290                 295                 300

Gly Ile Ile Leu Leu Val Ile Gly Ala Gly Val Phe Lys Gln Val
305                 310                 315                 320

Leu Val Asp Ser Gly Val Gly Pro Ala Leu Gly Asp Ala Val Ala Gly
                325                 330                 335

Ala Gly Leu Pro Val Ala Val Ala Cys Phe Ile Leu Ala Gly Ala Val
            340                 345                 350

Arg Ile Ile Gln Gly Ser Ala Thr Val Ala Cys Leu Thr Ala Val Gly
            355                 360                 365

Leu Ile Met Pro Val Ile Glu Pro Leu His Tyr Ser Gly Ala Gln Leu
    370                 375                 380

Ala Ala Leu Ser Val Cys Ile Gly Gly Gly Ser Ile Ile Phe Ser His
385                 390                 395                 400

Val Asn Asp Ala Gly Phe Trp Leu Phe Gly Arg Phe Thr Gly Ala Ser
                405                 410                 415

Glu Ala Glu Thr Leu Lys Thr Trp Thr Leu Met Glu Thr Ile Leu Gly
            420                 425                 430

Thr Ser Gly Gly Ile Ile Gly Met Leu Ala Phe Trp Leu Leu Ser
            435                 440                 445

<210> SEQ ID NO 3
<211> LENGTH: 1320
<212> TYPE: DNA
<213> ORGANISM: Pantoea citrea

<400> SEQUENCE: 3
atgccaatta caataatagc gctcggggta atactgctgc tggtcctgat gattgttttc    60
```

-continued

```
aaggccaacg cttttttatc tctgattttt gtctccatcg tcgtaggtat agccgaaggg    120
atgacaccgt tgcaggccct ggcttctgta caaaaagggg ttggcggtac tctgggcagc    180
cttgcgatga ttcttggttt tggtgccatg ctcggtaagc tggtgtcaga taccggggcc    240
gcccaacggg tggcgaccac gttgattgcg gcttttggta acagcgggt gcaatgggct     300 ctgatggtga cagggctgat tgtcgggctg gccatgtttt atgaaattgg ttttgtcctg    360
ttgttaccgc tggtgtttac cgtggtggcc gccgccggta tgccattact gtatgtgggg    420
ctgccgatgg tggctgcatt gtcagtgacc cattgcttcc tgcctccgca cccggggccg    480
acggcgatcg ccgctatctt cggggccaat ctgggtacca cactgttgta tggcataatt    540
attaccctgc aacggtgat tgtggccggt ccggtatttt ctaagttcct aaaaaacttt     600
gaaaaagaac cgccggaagg ctgtataac cccaaaattt cgccgaaca tgagttgccc      660 ggattcgcta ttagtatatt tgctgcagtc atcccggtga tccttatggc gattgccgca    720 gttttgaac tcacaactcc gaaagagaat ccgctccgtc agttttcga atttattggt      780 aaccctgcga tcgcgctgtt tattgccgtg gtgatcgccg tatttaccct cggattgcgc    840
aatggccgga aaatgggcga agtcatggag atgtgcagct cctcaatttc gtcaattgcc    900
atgattgtat ttatcattgc cggtggcggg gcatttaaac aagtcctggt ggacagtggg    960
gtgggcgatt ttatcgcagg aatgatgaaa ggatcgtcat tgtcgccact attgatgtgc   1020
tggaccgtgg cggcaatgct gcgagttgcg ttgggatcag ccacagtagc ggcgattact   1080
accgcgggta ttgtcactcc gattatcgcg gtgactcacg cagaccctgc actaatggtg   1140
ttggcggtag ggtctggtag cgtgatcgcc tcgcatgtta atgaccccgg tttctggtta   1200
ttcaaaggct actttaatct gagcgtgact gaaacactga aaacctggac tgtgatggaa   1260
acactgattt cggtgatggg tctggccgga gtccttattc ttaactcagt actgcactaa   1320
```

<210> SEQ ID NO 4
<211> LENGTH: 439
<212> TYPE: PRT
<213> ORGANISM: Pantoea citrea

<400> SEQUENCE: 4

```
Met Pro Ile Thr Ile Ala Leu Gly Val Ile Leu Leu Val Leu
 1               5                  10                  15

Met Ile Val Phe Lys Ala Asn Gly Phe Leu Ser Leu Ile Phe Val Ser
                20                  25                  30

Ile Val Val Gly Ile Ala Glu Gly Met Thr Pro Leu Gln Ala Leu Ala
            35                  40                  45

Ser Val Gln Lys Gly Val Gly Gly Thr Leu Gly Ser Leu Ala Met Ile
        50                  55                  60

Leu Gly Phe Gly Ala Met Leu Gly Lys Leu Val Ser Asp Thr Gly Ala
65                  70                  75                  80

Ala Gln Arg Val Ala Thr Thr Leu Ile Ala Ala Phe Gly Lys Gln Arg
                85                  90                  95

Val Gln Trp Ala Leu Met Val Thr Gly Leu Ile Val Gly Leu Ala Met
                100                 105                 110

Phe Tyr Glu Ile Gly Phe Val Leu Leu Pro Leu Val Phe Thr Val
            115                 120                 125

Val Ala Ala Ala Gly Met Pro Leu Leu Tyr Val Gly Leu Pro Met Val
        130                 135                 140

Ala Ala Leu Ser Val Thr His Cys Phe Leu Pro Pro His Pro Gly Pro
145                 150                 155                 160
```

```
Thr Ala Ile Ala Ala Ile Phe Gly Ala Asn Leu Gly Thr Thr Leu Leu
                165                 170                 175
Tyr Gly Ile Ile Ile Thr Leu Pro Thr Val Ile Val Ala Gly Pro Val
            180                 185                 190
Phe Ser Lys Phe Leu Lys Asn Phe Glu Lys Glu Pro Pro Glu Gly Leu
        195                 200                 205
Tyr Asn Pro Lys Ile Phe Ala Glu His Glu Leu Pro Gly Phe Ala Ile
    210                 215                 220
Ser Ile Phe Ala Ala Val Ile Pro Val Ile Leu Met Ala Ile Ala Ala
225                 230                 235                 240
Val Phe Glu Leu Thr Thr Pro Lys Glu Asn Pro Leu Arg Gln Phe Phe
                245                 250                 255
Glu Phe Ile Gly Asn Pro Ala Ile Ala Leu Phe Ile Ala Val Val Ile
            260                 265                 270
Ala Val Phe Thr Leu Gly Leu Arg Asn Gly Arg Lys Met Gly Glu Val
        275                 280                 285
Met Glu Met Cys Ser Ser Ser Ile Ser Ser Ile Ala Met Ile Val Phe
    290                 295                 300
Ile Ile Ala Gly Gly Ala Phe Lys Gln Val Leu Val Asp Ser Gly
305                 310                 315                 320
Val Gly Asp Phe Ile Ala Gly Met Met Lys Gly Ser Ser Leu Ser Pro
                325                 330                 335
Leu Leu Met Cys Trp Thr Val Ala Ala Met Leu Arg Val Ala Leu Gly
            340                 345                 350
Ser Ala Thr Val Ala Ala Ile Thr Thr Ala Gly Ile Val Thr Pro Ile
        355                 360                 365
Ile Ala Val Thr His Ala Asp Pro Ala Leu Met Val Leu Ala Val Gly
    370                 375                 380
Ser Gly Ser Val Ile Ala Ser His Val Asn Asp Pro Gly Phe Trp Leu
385                 390                 395                 400
Phe Lys Gly Tyr Phe Asn Leu Ser Val Thr Glu Thr Leu Lys Thr Trp
                405                 410                 415
Thr Val Met Glu Thr Leu Ile Ser Val Met Gly Leu Ala Gly Val Leu
            420                 425                 430
Ile Leu Asn Ser Val Leu His
        435

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
ttgctgcatc aacagtcgga g                                              21

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gttattccgg cacaagcagc c                                              21

<210> SEQ ID NO 7
```

```
<211> LENGTH: 19
<212> TYPE: DNA
<213> ORGANISM: Artificial Sequence
<220> FEATURE:
<223> OTHER INFORMATION: primer

<400> SEQUENCE: 7
gcgctggcca cggtagtta                                                  19

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
cgaagaagcc gccaggatgt ta                                              22

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
ccggcggtat tatttgttt ctga                                             24

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
gaaagttgga acctcttacg tgccg                                           25

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
acaacagtac tgcgatgagt ggcag                                           25

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
taggtatagc cgaagggatg acac                                            24

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
```

```
agagcctttg cctttgataa cagc                                              24
```

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14

```
ctttggccgc tgaactgacg agat                                              24
```

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15

```
tataaacaga aaaggacaga tgag                                              24
```

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16

```
taccagccgc ataccgatac acc                                               23
```

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17

```
ccggttattc gcgttatgtg                                                   20
```

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18

```
tgtcagccgt taagtgttcc tgtg                                              24
```

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19

```
cagttcaacc tgttgatagt acg                                               23
```